United States Patent
Freed et al.

(10) Patent No.: US 9,201,158 B2
(45) Date of Patent: Dec. 1, 2015

(54) ESTIMATING AND DISPLAYING MOLECULAR SIZE INFORMATION OF A SUBSTANCE

(75) Inventors: Denise E. Freed, Newton Highlands, MA (US); Lukasz J. Zielinski, Houston, TX (US); Yi-Qiao Song, Newton Center, MA (US); Marcus Donaldson, Somerville, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 941 days.

(21) Appl. No.: 13/357,378

(22) Filed: Jan. 24, 2012

(65) Prior Publication Data

US 2013/0187648 A1    Jul. 25, 2013

(51) Int. Cl.
| | |
|---|---|
| G01V 3/00 | (2006.01) |
| G01V 3/32 | (2006.01) |
| G01N 24/08 | (2006.01) |
| G01R 33/44 | (2006.01) |

(52) U.S. Cl.
CPC ............... *G01V 3/32* (2013.01); *G01N 24/081* (2013.01); *G01R 33/448* (2013.01)

(58) Field of Classification Search
CPC ........................................................ G01V 3/00
USPC ................... 324/303, 306, 307, 309
See application file for complete search history.

(56) References Cited

U.S. PATENT DOCUMENTS

| | | | |
|---|---|---|---|
| 5,023,551 A |  | 6/1991 | Kleinberg et al. |
| 5,291,137 A | * | 3/1994 | Freedman ................... 324/303 |
| 6,462,542 B1 |  | 10/2002 | Venkataramanan et al. |
| 6,859,032 B2 |  | 2/2005 | Heaton et al. |
| 6,883,702 B2 | * | 4/2005 | Hurlimann et al. ........... 324/303 |
| 7,718,434 B2 |  | 5/2010 | Freed |
| 8,093,056 B2 | * | 1/2012 | Ganesan ......................... 436/28 |

OTHER PUBLICATIONS

Freed, et al., "Scaling Laws for Diffusion Coefficients in Mixtures of Alkanes", Physical Review Letters, vol. 94 (6), Feb. 17, 2005, 4 pages.
Freed, Denise E., "Dependence on chain length of NMR relaxation times in mixtures of alkanes", Journal of Chemical Physics, vol. 126 (17), 2007, 10 pages.
Freed, Denise E. , "Temperature and pressure dependence of the diffusion coefficients and NMR relaxation times of mixtures of alkanes", J. Phys. Chem. B. vol. 113 (13), 2009, pp. 4293-4302.
(Continued)

*Primary Examiner* — Louis Arana

(57) ABSTRACT

Estimating and displaying information about the size of molecules within a substance from nuclear magnetic resonance (NMR) maps and/or logs. Methods include utilizing a relationship between the molecular size (e.g., mean chain length), and either a moment of diffusion or a relaxation distribution, to create a scale on a two-dimensional map. In one case, applying the relationship between the molecular size, and either a moment of diffusion or a relaxation distribution, to one-dimensional diffusion or relaxation distributions for the purpose of estimating the mean chain length of molecules within the substance. In another case, a method includes determining mean chain lengths of molecules within a substance and providing a one-dimensional NMR log showing the mean chain lengths at a plurality of depths. In some cases, the NMR log includes actuatable regions for examining two-dimensional NMR maps or chain length distributions of the substance corresponding with distinct depths of the substance.

28 Claims, 23 Drawing Sheets

(56) References Cited

OTHER PUBLICATIONS

Freedman, et al., "Fluid Characterization using Nuclear Magnetic Resonance Logging", Petrophysics, vol. 45 (3), 2004, pp. 241-250.

Freedman, et al., "Hydrocarbon Saturation and Viscosity Estimation From Nmr Logging in the Belridge Diatomite", The Log Analyst, vol. 38 (2), 1997, pp. 44-72.

Helbaek, et al., "Self-Diffusion Coefficients of Methane or Ethane Mixtures with Hydrocarbons at High Pressure by NMR", J. Chem. Eng. Data, vol. 41, 1996, pp. 598-603.

Hurlimann, et al., "Diffusion-Editing: New NMR Measurement of Saturation and Pore Geometry", SPWLA 43rd Annual Logging Symposium, 2002, 14 pages.

Hurlimann, et al., "Hydrocarbon Composition From NMR Diffusion and Relaxation Data", Petrophysics, vol. 50 (2), 2009, pp. 116-129.

Kleinberg, et al., "NMR properties of reservoir fluids", Log Analyst, vol. 37 (6), 1996, pp. 20-32.

Kleinberg, Robert L., "Well Logging", Encyclopedia of NMR, Wiley, New York, 1996, pp. 4960-4968.

Minh, et al., "Using the Continuous NMR Fluid Properties Scan to Optimize Sampling With Wireline Formation Testers", SPE 115822-SPE Annual Technical Conference and Exhibition, Denver, Colorado, Sep. 21-24, 2008, 14 pages.

Mutina, et al., "Correlation of Transverse and Rotational Diffusion Coefficient: A Probe of Chemical Composition in Hydrocarbon Oils", Journal of Physical Chemistry A, vol. 112 (15), 2008, pp. 3291-3301.

Venkataramanan, et al., "Mellin transform of CPMG data", Journal of Magnetic Resonance, vol. 206 (1), Sep. 2010, pp. 20-31.

White, et al., "Continuous Characterization of Multiple Fluids in a North Sea Gas Condensate Reservoir by Integrating Downhole NMR With Downhole Sampling", 49th Annual Logging Symposium, Austin, Texas, May 25-28, 2008, 9 pages.

Zittel, et al., "Reservoir Crude Oil Viscosity Estimation From Wireline NMR Measurements—Rajasthan, India", SPE 101689-SPE Reservoir Evaluation & Engineering, vol. 11 (3), Jun. 2008, pp. 545-553.

\* cited by examiner

ESTIMATING AND DISPLAYING MOLECULAR SIZE INFORMATION OF A SUBSTANCE

TECHNICAL FIELD

This invention relates to analysis of substances. More particularly the invention relates to analysis of substances using nuclear magnetic resonance (NMR).

BACKGROUND

General background of nuclear magnetic resonance (NMR) well logging is set forth, for example, in U.S. Pat. No. 5,023,551. Briefly, NMR well logging includes generating a magnetic field within a borehole (e.g., under the earth's surface), applying a series of electromagnetic pulses to the area around the borehole, and measuring signals received in response to those pulses to determine characteristics of the area proximate to the borehole. Conventional characteristics of the area measured during NMR well logging include longitudinal ($T_1$) and transverse ($T_2$) relaxation times, as well as diffusion coefficients of the fluid inside the area. In addition to these one-dimensional (1D) measurements of relaxation times and diffusion coefficients, NMR logs can provide two-dimensional (2D) maps showing the correlation between diffusion and relaxation times (D-$T_2$ or D-$T_1$ maps) and the correlation between longitudinal and transverse relaxation times ($T_1$-$T_2$ maps). These measurements are typically used to determine rock properties such as porosity and permeability, as well as fluid properties such as the saturation of oil, water and gas. In some cases, these measurements are used to determine the viscosity of the oil. Often on these logs, particularly with 2D maps, the water, gas and oil signals can be distinguished, which aids in determining the saturations of the oil, gas and water. In addition, by looking at the position of the oil signal on the map, one can obtain an estimate of the viscosity of the oil, due to various correlations between log mean relaxation times and viscosity.

At present, conventional techniques known by the inventors do not use the D-$T_1$, D-$T_2$ or $T_1$-$T_2$ maps to estimate the mean size of the molecules in the oil, or other related properties of the oil. This is because no straightforward correlation exists between the molecule size in the mixture, and the diffusion coefficients and relaxation times. This is in contrast to viscosity, where the correlation between viscosity and relaxation times enables one to estimate the viscosity from the 1D and 2D maps. Because the diffusion coefficients and relaxation times for a molecule in a mixture depend upon properties of the other molecules in that mixture, it may not be possible to determine the size of that molecule of interest without knowledge about characteristics of the remaining mixture. Additionally, the diffusion coefficients and relaxation times are both pressure and temperature dependent, making it even more difficult to use this information to deduce molecule sizes in a mixture.

SUMMARY

In contrast to prior approaches, illustrative embodiments are directed to estimating and displaying information about the molecular size (e.g., mean chain length, chain length distribution, a binned molecular size distribution, hydrodynamic radius and/or hydrocarbon number) of a substance using a nuclear magnetic resonance (NMR) map and/or NMR log. Various embodiments of the invention include utilizing a relationship between the size of molecules within a substance, and either a diffusion and/or relaxation coefficient, to create a scale on a 2D map. The map can be used to estimate a moment of diffusion of the substance. Various embodiments include using the scale on the map and the estimated moment of diffusion to estimate the size (e.g., mean chain length) of molecules within the mixture. Other embodiments include applying the above-noted relationship to 1D diffusion or relaxation distributions. These estimates of the mean chain length of molecules within the substance (e.g., oil) provide a measure of basic properties of that substance. Some additional embodiments include providing a 1D NMR log showing mean chain lengths of molecules within a substance at a plurality of depths. The 1D NMR log can include actuatable regions corresponding to the depths which can be actuated to provide a 2D NMR map or a chain length distribution of the substance at that depth.

Various embodiments are directed to a method including determining a mean chain length scale on an NMR map of molecules within a substance. The method further includes generating a size estimate of the molecules within the substance using the mean chain-length scale and the NMR map.

Further illustrative embodiments are directed to a method including: determining a molecular size of molecules within a substance based upon NMR signals, generating a plot of the molecular size of the molecules of the substance as a function of a sampling parameter (e.g., a depth of the substance in situ, a time of sampling and/or a batch identifier) of the substance, and providing that plot for display.

Various other embodiments are directed to a method for determining a characteristic of a substance. The method includes obtaining nuclear magnetic resonance (NMR) signals about the substance, and calculating the mean chain-length of molecules within the substance based upon the NMR signals. The method further includes providing a one-dimensional (1D) nuclear magnetic resonance (NMR) log representing a calculated mean chain length of the molecules within the substance at a plurality of depths of the substance. The 1D NMR log includes an actuatable region at each of the plurality of depths for providing at least one of a two-dimensional (2D) NMR map or a chain length distribution of the substance at the each of the plurality of depths.

BRIEF DESCRIPTION OF THE DRAWINGS

Further features and advantages will become more readily apparent from the following detailed description when taken in conjunction with the accompanying drawings.

Figure 1:
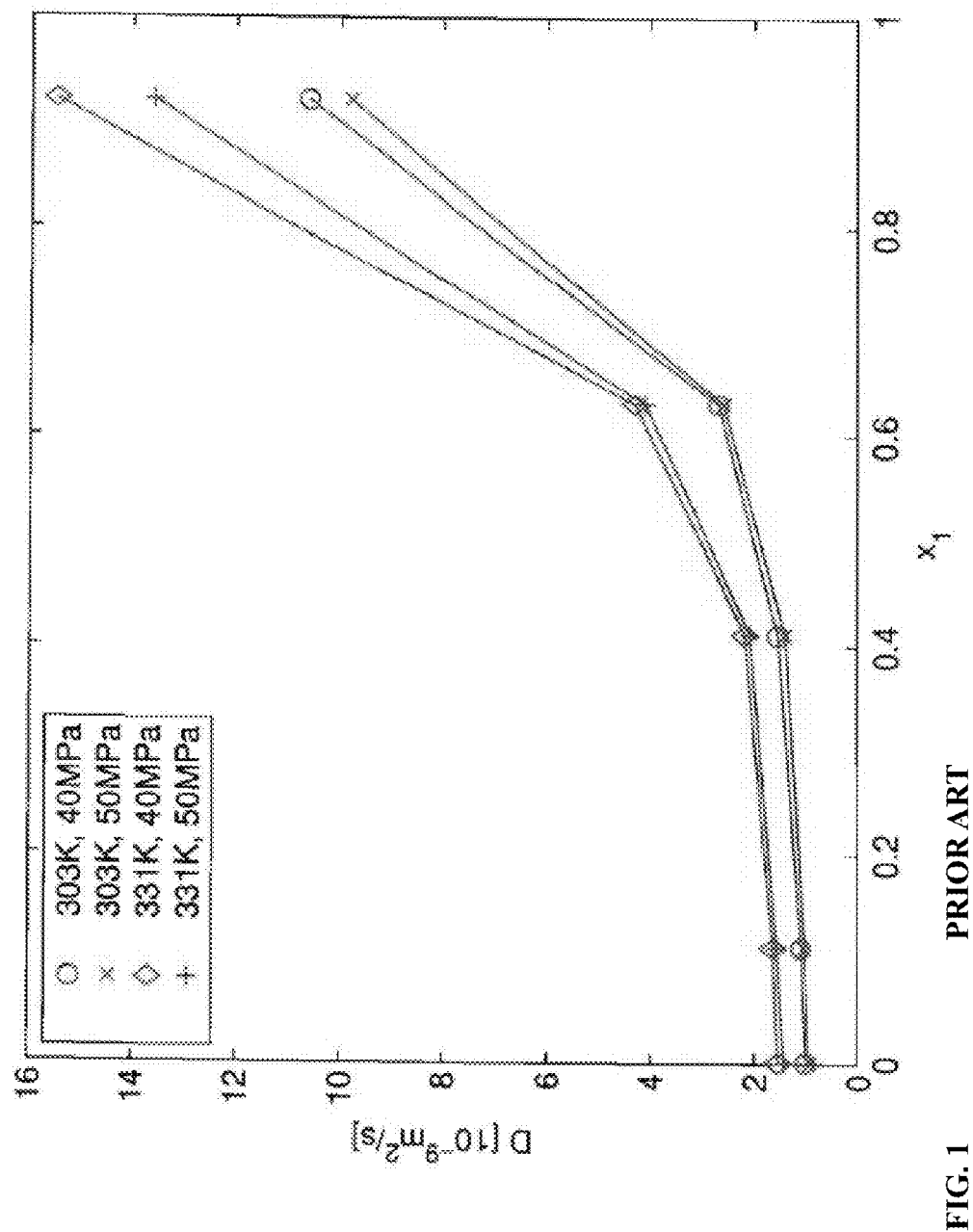
FIG. 1 shows a plot illustrating the self-diffusion coefficient of decane in binary mixtures with methane as a function of mole fraction of methane, as is conventionally known.

It is understood that the drawings of the disclosure are not necessarily to scale. The drawings are intended to depict only typical aspects of the disclosure, and therefore should not be considered as limiting the scope of the invention.

DESCRIPTION OF ILLUSTRATIVE EMBODIMENTS

As noted herein, the invention provides solutions for estimating and displaying information about the size of molecules within a substance using the NMR maps and/or logs. Various embodiments of the invention include utilizing a relationship, between the mean chain length and a moment of diffusion and/or a relaxation distribution, to create a scale on a 2D map. This scale can provide an estimate of the molecular size (e.g., mean chain length, hydrodynamic radius and/or hydrocarbon number) of the molecules within the mixture. Other embodiments include applying the above-noted relationship to 1D diffusion or relaxation distributions. Additional embodiments include providing a 1D nuclear magnetic resonance (NMR) log showing mean chain lengths of a substance at a plurality of depths. In various additional or alternative embodiments, a 1D NMR log is provided including actuatable regions corresponding to depths of the substance, where each of the actuatable regions can be actuated to provide a 2D NMR map of the molecules within the substance at that depth.

In various embodiments of the invention, the techniques described herein can be performed in order to determine characteristics of a substance in situ, e.g., in its natural environment. In these cases, using the example substances of oil, gas, or oil-based mud, various embodiments of the invention are directed toward determining a molecular size of the substance from data obtained while that substance is in the earth or surrounded by a rock formation. In various other embodiments of the invention, the techniques described herein can be performed in order to determine characteristics of a substance outside of its natural environment. In these cases, the data used to determine the molecular size of the substance can be obtained while the substance is outside of its natural environment. For example, the data can be obtained during a flowline analysis process, a core analysis (e.g., a multi-phase analysis), a down-hole fluid analysis process, or in a laboratory.

Such estimates of the molecular size of the substance (or, as used interchangeably herein, the mean chain length, hydrodynamic radius, or hydrocarbon number of the substance) provide a measure of basic properties of that substance. Where the estimates are made from log data such as nuclear magnetic resonance (NMR) log data, they can provide basic information about the substance present within a larger structure, e.g., oil inside of a rock matrix. These estimates can be combined with viscosity estimates to provide a preliminary characterization of the substance. As noted, in contrast to viscosity, the mean chain length is a property of the substance that is independent of temperature and pressure. The mean chain length estimates can help in identifying the type of substance, e.g., the type of oil such as condensate, light, or black oil. These estimates can further help in identifying which NMR signal is the native oil signal, as opposed to an oil-based mud (OBM) signal or a water signal. When these estimates are made at several depths, they can be used to identify gradients in the oil composition and compartmentalization of the oil at the various depths.

The mean chain length estimates also can be used to determine at which depths the characterization of the oil and gas should be made more quantitative. This can be performed by conducting a more quantitative analysis of the NMR data, or by acquiring more NMR data or other data, such as formation tester measurements. In addition, the mean chain length estimates found with NMR data can be directly compared to the fluid composition found from a down hole fluid analysis (DFA) performed with the formation tester tools (although these latter measurements are generally sensitive to the smaller molecules).

The diffusion coefficients and relaxation times of a molecule in a mixture depend on the composition of the entire mixture. For this reason, when measuring the diffusion coefficient of a molecule in a mixture, it can be difficult to determine molecular size without knowing more about the entire mixture. For example, FIG. 1 shows the self-diffusion coefficient of decane in binary mixtures with methane as a function of mole fraction of methane, $x_1$, for temperatures of T=303K and 331K and pressures of P=40 MPa and 50 MPa, as is known conventionally. As can be seen in FIG. 1, the diffusion of decane varies by about a factor of 10 as the methane content is varied. When the temperature is varied by about 10%, the diffusion coefficients change by about 50%. In oil reservoirs, the temperatures can be significantly higher, resulting in even larger differences between the diffusion coefficients at ambient temperatures, and those in the reservoirs. The transverse relaxation times show similar variations with composition and temperature. Thus, reading off the diffusion or relaxation times from a diffusion distribution, a relaxation distribution or 2-D maps will not necessarily indicate the size of the molecules without taking into account the effect of all the other molecules in the mixture.

The inventors have discovered that by restrictively searching for the molecular size, and in some particular embodiments, mean chain length, the relationship between a moment of the diffusion and relaxation times and this mean size can be determined. This relationship makes accurately estimating the average molecular size from these distributions possible. For mixtures of alkanes and crude oils high in saturates, the diffusion coefficient $D_i$, the longitudinal relaxation time $T_{1i}$, and the transverse relaxation $T_{2i}$ of the $i^{th}$ component can be represented in terms of the chain length or carbon number of this component, $N_i$ and the molar mean chain length of the mixture, N, given by Equation (1):

$$\overline{N} = \sum_i x_i N_i,$$

where $x_i$ is the mole fraction of molecules with chain length $N_i$. Then $D_i$ and $T_{1,2i}$ are given by Equations (2) and (3), respectively:

$$D_i = A N_i^{-\nu} \overline{N}^{-\beta},$$

and $$T_{1i} = T_{2i} = B N_i^{-\kappa} \overline{N}^{-\gamma},$$

where the exponents v and k are given by v=0.7 and k=1.24 in this particular example. The exponents β and γ are temperature dependent, and the coefficients A and B are also temperature and pressure dependent. Parameters A, B, β and γ are approximated by A=3.5×10$^{-7}$ m$^2$/s, B=672 s, β=1.73 and γ=1.25 at 25° C. and atmospheric pressure in this particular example. It is understood that the values of v, k, A, B, β and γ denoted herein are not constant values, and could vary depending upon a number of factors, including, e.g., temperature, pressure and the characteristics of the oil.

Equations (2) and (3) show that the diffusion coefficients of each molecule depend on the mean chain length of the mixture. This indicates that as the composition of the mixture is varied, the mean chain length will vary, and the diffusion coefficient and relaxation time of the $i^{th}$ component, $D_i$ and $T_{1,2i}$ will vary. Focusing on the mean chain length, Equations (2) and (3) can be inverted to obtain Equations (4) and (5), respectively:

$$\overline{N} = [A\langle D^{1/\nu}\rangle_w^{-\nu}]^{\frac{1}{\nu+\beta}},$$

and, $$\overline{N} = [B\langle T_{1,2i}^{1/\kappa}\rangle_w^{-\kappa}]^{\frac{1}{\kappa+\gamma}},$$

where $\langle D^{1/\nu}\rangle_w$ is the mean, with respect to the weight fraction, of $D^{1/\nu}$, and $\langle T_{1,2i}^{1/\kappa}\rangle_w$ is defined similarly. The NMR measurements are sensitive to the number of protons $f(D_i)$ and $f(T_{1,2i})$ with a particular diffusion coefficient $D_i$ or relaxation time $T_{1,2i}$, respectively, not necessarily the weight fractions, $w(D_i)$ and $w(T_{1,2i})$. For linear and branched alkanes, they are related according to Equation (6):

$$w(D_i) = \frac{\dfrac{14N_i+2}{2N_i+2}f(D_i)}{\displaystyle\sum_j \frac{14N_j+2}{2N_j+2}f(D_j)}.$$

In this case, the weight fraction $w(D_i)$ is approximately equal to the proton fraction $f(D_i)$ as long as $N_i$ is large enough. Thus, for $N_i$ greater than about 3, for a good approximation we can use the proton fraction and set Equation (7):

$$\langle D^{1/\nu}\rangle_w \approx \sum_i D_i^{1/\nu} f(D_i)\Delta D_i = \langle D^{1/\nu}\rangle_p.$$

Various embodiments of the present invention also apply this approximation to crude oils with saturates and aromatics. The mean chain length can be directly related to the $(1/\nu)^{th}$ moment of D, averaged with respect to the proton fraction. If the signal for the oil or gas has been identified on a 1D or 2D distribution, the inventors have discovered it is possible to estimate an average moment of diffusion ($D_{ave}$) or average relaxation time ($T_{1,2ave}$). For example, $D_{ave}$ or $T_{1,2ave}$ can be estimated, respectively, as $D_{ave} = \langle D^{1/\nu}\rangle_p$ or $T_{1,2ave} = \langle T_{1,2i}^{1/\kappa}\rangle_p$ by looking at the distribution of the oil or gas. This can be performed visually as is known conventionally, in a similar manner in which one visually estimates the mean log diffusion or relaxation from NMR maps.

Further, according to embodiments of the invention, and in particular with respect to Equations (4) and (5), after determining $D_{ave}$ (average moment of diffusion) or $T_{ave}$ (average relaxation time) the value of the mean chain length can be calculated, as provided by Equations (8) and (9), respectively:

$$\overline{N} = (AD_{ave}^{-1})^{\frac{1}{\nu+\beta}},$$

and $$\overline{N} = (BT_{ave}^{-1})^{\frac{1}{\kappa+\gamma}}.$$

Figure 2:
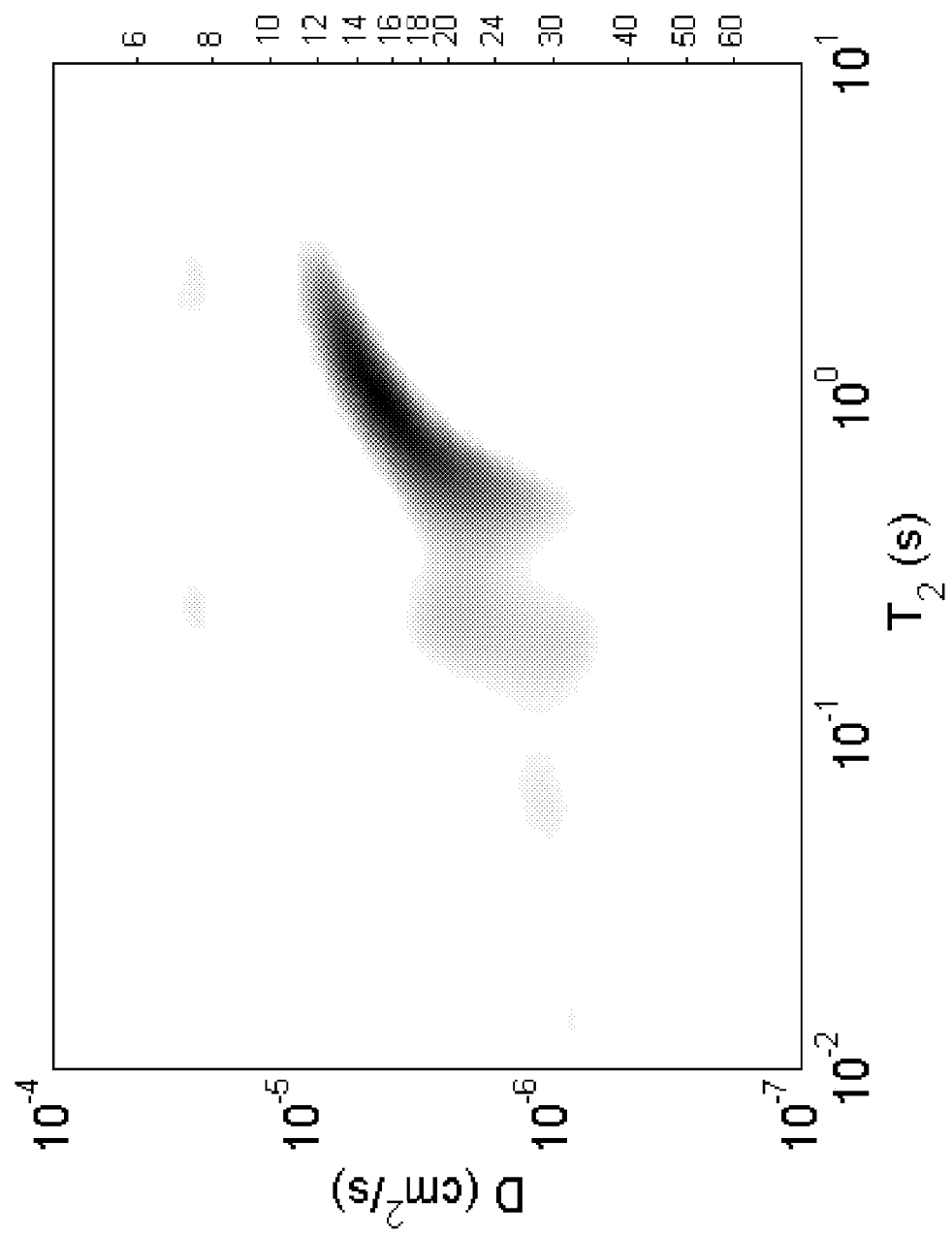
FIGS. 2-8 show example NMR maps illustrating various scaling features according to embodiments of the disclosure.
Figure 3:
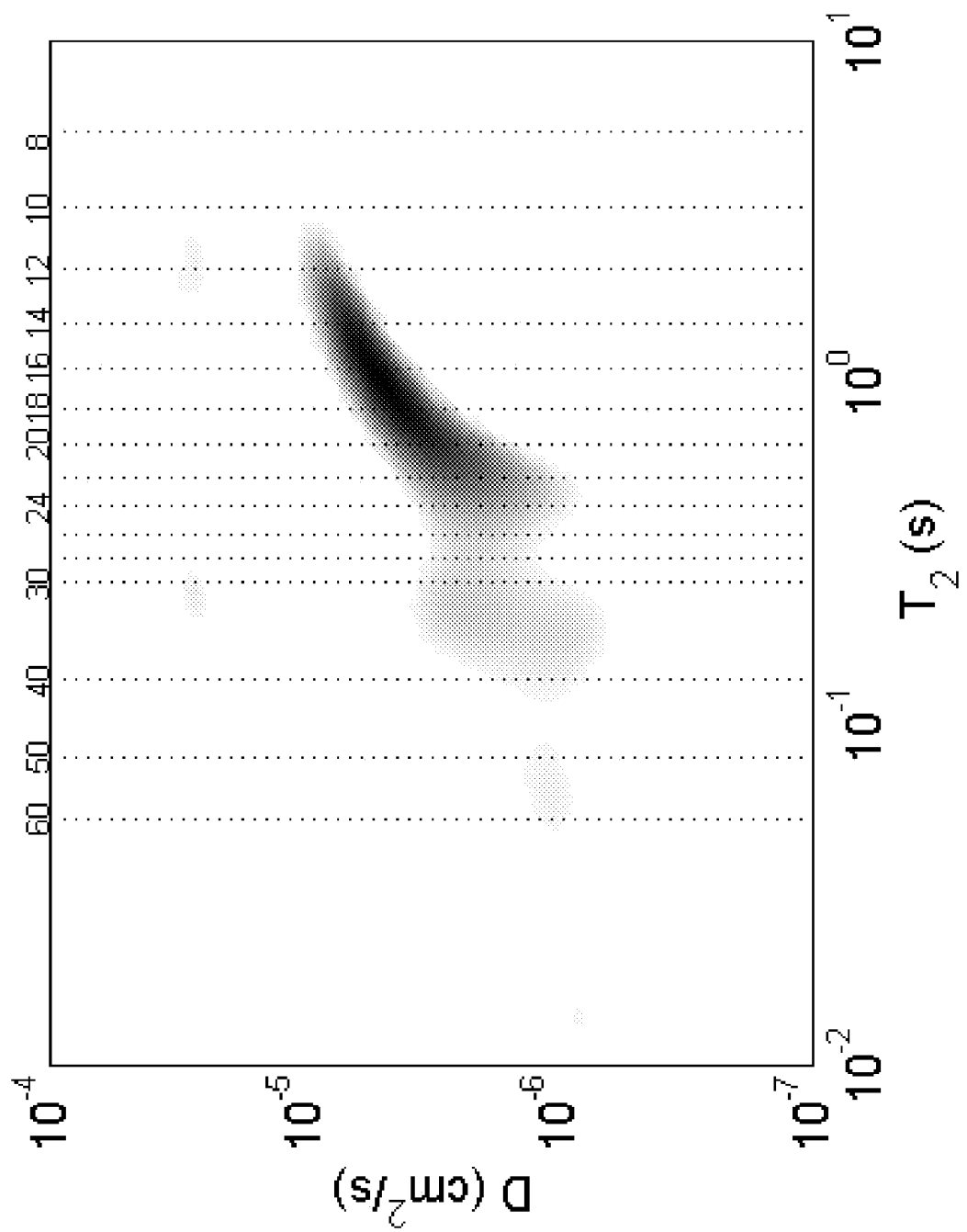

As described further herein with respect to FIGS. 2-3, Equations (8)-(9) can be utilized in some embodiments to apply a scale (e.g., via notched indicators) on 2-D NMR maps.

As described herein, various embodiments of the invention can include methods such as determining a mean chain length scale on a nuclear magnetic resonance (NMR) map of a substance, and generating an estimate of a mean chain length of the substance using the mean chain-length scale and the diffusion-relaxation map. The NMR map in this example is based upon data about the substance obtained in situ, e.g., in a natural environment such as within the earth. In some cases, the data about the substance is obtained during one of a logging-while-drilling (LWD) or a wireline drilling application, and is obtained via conventional NMR methods during one of these processes. However, in various other embodiments, the data about the substance could be obtained during a flow-line analysis process, a core analysis, a down-hole fluid monitoring process and/or during a laboratory analysis.

In some embodiments, the substance includes at least one of an oil (e.g., a variety of crude oil), a gas or an oil-based mud. Where the substance is in-earth, the substance can further include rock, water, or other components conventionally found within a drilling environment. These substances should not be considered limiting of the invention, as various embodiments described herein can be applicable to any number of NMR methods used to explore characteristics of substances, e.g., in-situ or otherwise. For example, some embodiments of the invention could be applied in the medical field or other fields where NMR methods are employed. It is understood that advantages of aspects of the invention can be realized in the medical or other fields when determining characteristics of substances, e.g., in food applications such as analyzing properties of one or more food substances.

Various embodiments of the invention further include plotting the NMR map along with the mean chain-length scale for display, and in some cases, providing the NMR map and associated mean chain-length scale for display. The NMR map and associated scale can be displayed, e.g., at a user interface for review and analysis by human observer. In some cases, the user interface and process of displaying can be performed proximate the substance in situ, e.g., at a drilling site location. In other embodiments, however, the NMR map and associated scale can be displayed at a remote location distant from the substance in situ. In some cases, the method can include performing the plotting and the providing in separate processes. In some cases, display can be performed in real time, and in other cases, display can be performed at any other time after data has been acquired.

As described and shown herein with respect to the Figures, embodiments of the invention can include plotting the mean chain length scale on the NMR map in such a way that the scale is visually perceivable, e.g., to a user such as a human observer. This visually perceivable scale aids the observer in determining a mean chain length of the substance without substantial calculation or evaluation, thereby easing the process of determining the substance's mean chain length when compared to conventional methods.

In some embodiments, the NMR map includes a two-dimensional (2D) map such as a diffusion-relaxation (D-$T_1$, D-$T_2$) map and/or a relaxation-relaxation ($T_1$-$T_2$) map plotting NMR data about the substance obtained in-situ. In still other embodiments, the NMR map includes a one-dimensional (1D) distribution plot illustrating NMR data about the substance obtained in-situ.

Figure 4:
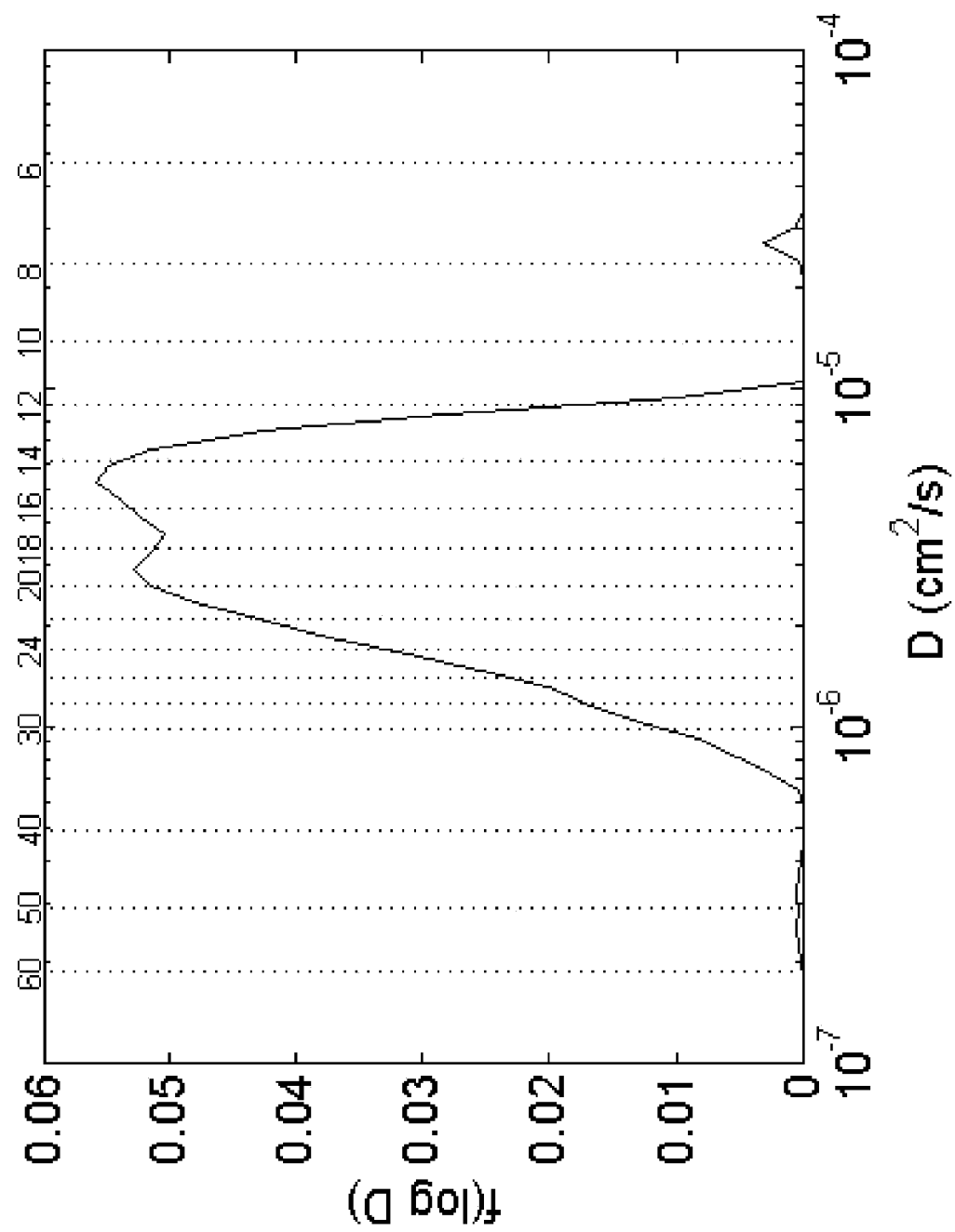

In various embodiments of the invention, methods for providing a scale on the 2D maps (D-$T_1$, D-$T_2$ or $T_1$-$T_2$) and 1D distributions are provided, where the scale can be used for estimating the mean chain length of the substance. In one particular embodiment, the scale is placed along the diffusion (or $T_2$ axis), with the notched indicators at values of $D_{ave}$ or $T_{ave}$ corresponding to a given mean chain length, N, according to Equations (8) and (9). For example, to determine the location of the notched indicator corresponding to a given N, this value of N can be put into Equations (8) and (9). These equations can then be used to solve for a $D_{ave}$ and a $T_{ave}$. The notch corresponding to the given N value can then be placed on the scale at the location where $D=D_{ave}$, when the scale is based on the diffusion coefficients, and where $T=T_{ave}$ when the scale is based on the relaxation times. Examples of these embodiments are illustrated in FIGS. 2-4.

In FIG. 2 and FIG. 3, an NMR (D-$\overline{T}_2$) map of an oil high in saturates is shown, with a mean chain length scale applied to each map according to various embodiments of the invention. The data used to construct these maps was obtained during an NMR process at atmospheric pressure and 30° C. In FIG. 2, a scale including values of R (mean chain length) (also referred to as N herein) is marked along the right-hand axis. Using FIG. 2, and by estimating where the mean diffusion coefficient value lies, one can read off the corresponding value of N from the right-hand axis. In this case, the peak of the distribution lies at about N=16, but the actual mean is at a lower diffusion coefficient, closer to N=17 or 18. It should be noted that because the FIG. 2 plot is on a log scale, estimating the mean diffusion coefficient includes estimating the mean of the logarithm of the diffusion coefficient. This yields an estimated mean chain length of $N_{est}$~17 or 18, compared with an N value of 15 found from a conventional gas chromatography (GC) approach and an N value of 16 found by using Equation (4) to calculate the mean chain length from the full diffusion distribution. The same oil plotted in FIG. 2 is plotted in the D-$T_2$ map in FIG. 3, but in this case, the values of N are marked along the top axis, and vertical lines are plotted to aid in determining the mean value of the relaxation time. In this case, the peak corresponds to an N value slightly higher than 16, with the mean likely approximately at 18. In this manner, the estimated mean chain length can be determined as $N_{est}$~18. FIG. 4 shows a diffusion distribution illustrating the projection of the D-$T_2$ map onto the diffusion axis from FIGS. 2-3. The values of N are plotted along the top axis, and vertical lines are again plotted to aid in estimating the mean diffusion coefficient and the N that corresponds to that mean diffusion coefficient. In this case, the estimated mean chain length N is again approximately 17 or 18.

Figure 5:
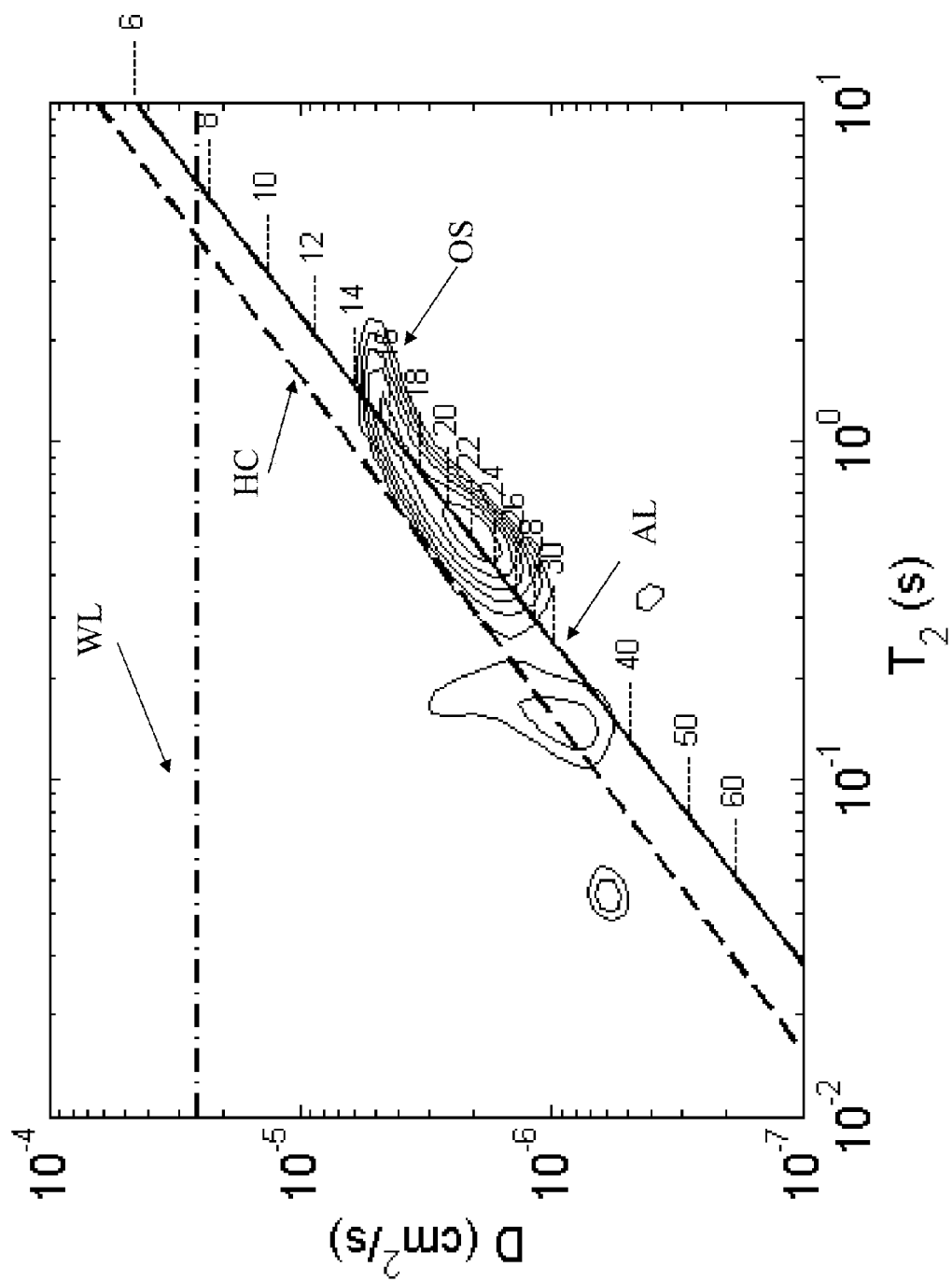
Figure 6:
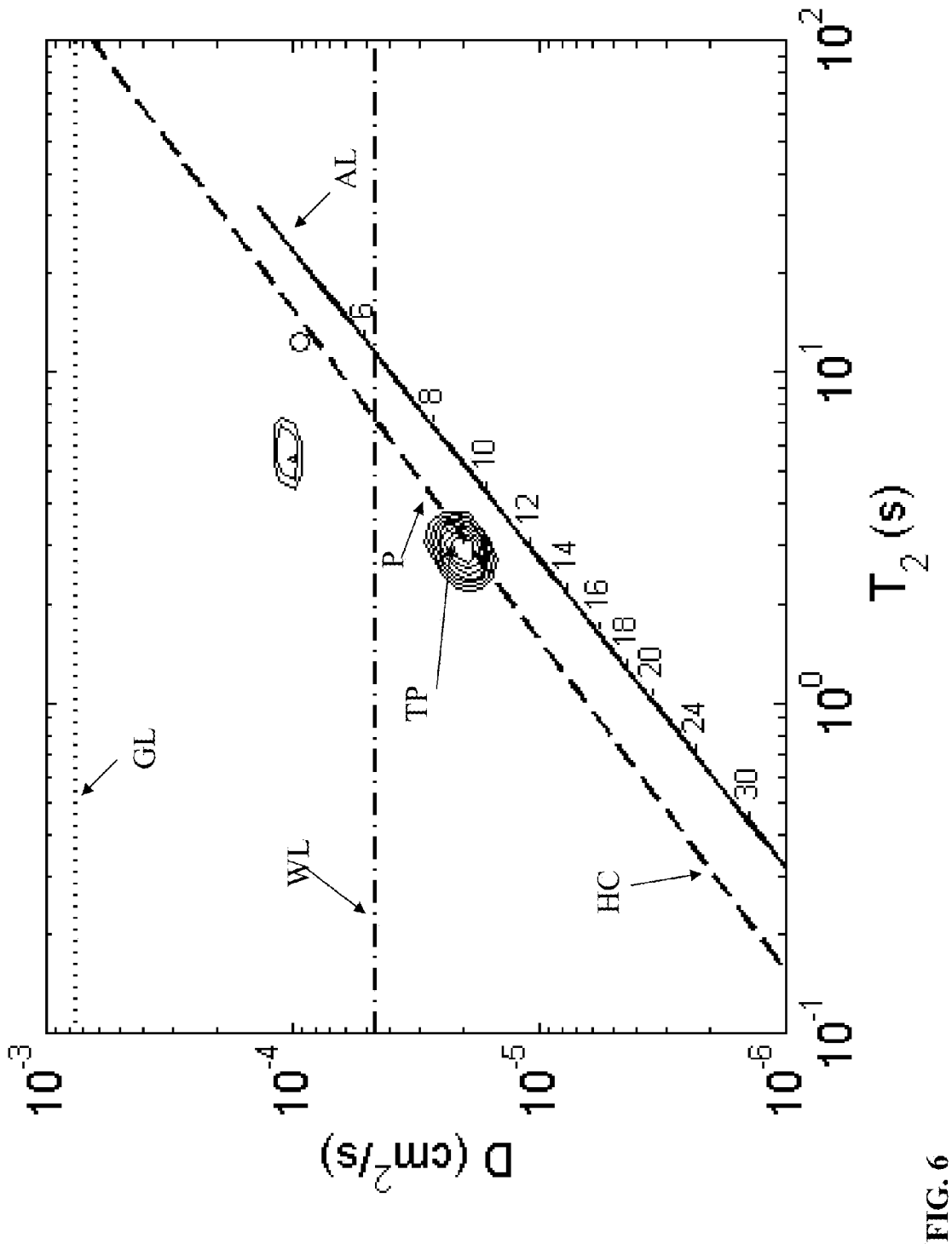
Figure 7:
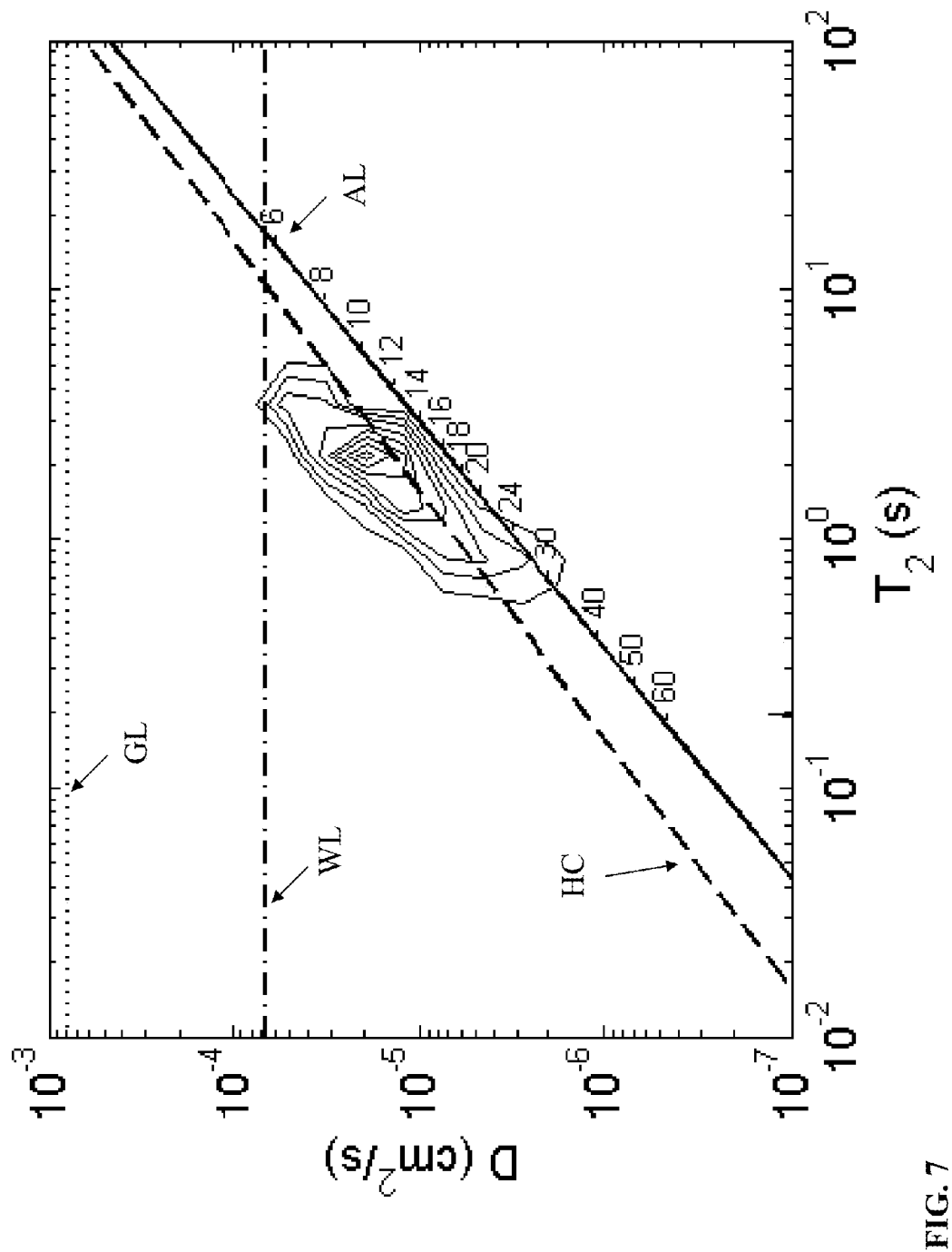

In another embodiment of the invention, described with respect to the D-$T_2$ maps of FIGS. 5-7, a method includes plotting a line on the 2-D map illustrating where the mean chain length of the mixture theoretically should lie, with indicators at the locations of particular mean chain lengths. In constructing this line, it is noteworthy that, according to Equations (2) and (3), the diffusion coefficient and relaxation time of the component with the mean chain length of the mixture is given by Equations (10) and (11), respectively:

$$D(\overline{N}) = A\overline{N}^{-(\nu+\beta)},$$

and, $$T_{1,2}(\overline{N}) = B\overline{N}^{-(\kappa+\gamma)}$$

Equations (10) and (11) are derived by setting $N_i = \overline{N}$ in Equations (2) and (3). Comparing Equations (10) and (11) with Equations (8) and (9) for the mean diffusion coefficient and relaxation time shows that $D_{ave}=D(\overline{N})$ and $T_{ave}=T_{1,2}(\overline{N})$. Combining this equation for $D_{ave}$ and $T_{ave}$ with Equations (10) and (11), and eliminating $\overline{N}$ from these equations, yields the following relationship between $D_{ave}$ and $T_{ave}$, illustrated by Equation (12):

$$D_{ave} = A\left(\frac{T_{ave}}{B}\right)^{\frac{\nu+\beta}{\kappa+\gamma}}.$$

For an oil satisfying Equations (2) and (3), it can be expected that the diffusion coefficient and relaxation time of the mean chain length in this oil mixture will fall along the line defined by $D_{ave}$. Equations (8) and (9) can be used to define a relationship between $D_{ave}$, $T_{ave}$ and N, and consequently, provide values for markers plotted along the $D_{ave}$ line which correspond to specified values of N.

As similarly noted in other methods according to embodiments, after plotting this $D_{ave}$ line, one aspect of the invention can include estimating the mean values of the diffusion coefficient and relaxation time. Following estimation of those mean diffusion coefficient values and relaxation times, a user (e.g., human or machine as described herein) can determine a corresponding location along the $D_{ave}$ line, and determine a mean chain length.

Similarly to the D-$T_2$ maps in FIGS. 2-3, for $T_1$-T2 maps, it can be expected that the substance (e.g., oil) signal will lie approximately along the line defined by $T_1=T_2$. In this embodiment, Equation (9) can define the location of markers corresponding to specific values of N along the $T_2$ line. These markers can be used to estimate the mean chain length of the substance. Several examples of D-$T_2$ maps are provided in FIGS. 5-7, each with a mean chain length scale plotted according to various aspects of the invention.

The first example, shown in FIG. 5, is of a "dead oil" at 30° C. and atmospheric pressure. As is known conventionally, a "dead oil" is an oil at sufficiently low pressure that it contains no dissolved gas, or a relatively thick oil or residue that has lost its volatile components. The line along which the water signal usually lies, known conventionally as the water line, is indicated by the line labeled WL. The line conventionally drawn for hydrocarbons is indicated by the line labeled HC. The alkane line defined approximately by Equation (12) is labeled AL. As shown, a substantial portion of the oil signal (OS) lies along this alkane line (AL). The mean relaxation and diffusion times are indicated at approximately N≈23, so $N_{est}$=23. The mean chain length found from applying Equation (4) to the entire diffusion distribution is approximately 20. Thus, the estimate value of N=23 is near the value calculated from the diffusion distribution, but systematically higher.

FIGS. 6-7 illustrate respective D-$T_2$ maps of a live oil sample, including a mean chain length scale plotted according to various embodiments of the invention. As is known conventionally, the term "live oil" refers to those oils containing dissolved gases such as methane. In particular, FIG. 6 illustrates a D-$T_2$ map of a mixture of hexadecane and methane at 60° C. and 5000 psi. This mixture was found to have an actual mean chain length of approximately 6.3, as determined by weighing the sample. A first horizontal line (GL) is a gas line, indicating where pure methane is expected to lie. A second horizontal line (WL) is the water line. A first diagonal line (HC) indicates the hydrocarbon line, and a second diagonal line (AL) indicates an alkane line. According to various aspects of the invention, a mean chain length scale for the live oil sample is plotted along the alkane line (AL) with N values marked along that line. In this example, the signal from hexadecane in the live oil has the following attributes: D≈2.0×10$^{-5}$ cm²/s and $T_2 \approx 2.9$ s. The signal from the dissolved methane in the live oil has the following attributes $D \approx 10 \times 10^{-5}$ cm²/s and $T_2 \approx 5.7$ s. The circular area denoted by label (TP) indicates a theoretical peak in the hexadecane and methane levels. In practice, the inventors have observed that in some cases the measured relaxation times are shorter than those predicted by theory, especially where the methane relaxation time ($T_2 \approx 5.7$ s) is greater than approximately a threshold dependent upon the specific NMR pulse sequence and NMR apparatus/tool motion. The inventors currently believe this relationship to be true because the NMR pulse sequence can have insufficient wait times and pulse trains to accurately measure such relatively long relaxation times. The agreement between the measurement and theory can be improved by increasing these times.

Further, as the processes responsible for the diffusion of methane are similar to those responsible for the diffusion of longer alkanes, the methane diffusion constant still satisfies Equation (2), but with $N_i^v$ replaced with the slightly larger $(N_i+1)^v$. The inventors note that the relaxation of methane, however, occurs by different processes than the relaxation of the longer alkanes, so the methane relaxation does not obey Equation (3). Instead, the methane relaxation has a significantly shorter relaxation time than that indicated by Equation (3). Thus, the actual methane signal would lie to the left of the alkane line (AL), instead of to its right, as would be predicted by Equation (3). As a result, the inventors have discovered the mean relaxation time and diffusion coefficient of the mixture lie to the left of the alkane line (AL), instead of along the line. The inventors have further discovered that the mean relaxation time will give an N value that is higher when compared to the N derived from the mean diffusion coefficient. According to some embodiments, the mean diffusion coefficient is used to obtain an estimate of N. To this end, a value of the mean diffusion coefficient (at about $2.8 \times 10^{-5}$ cm²/s) is estimated. The mean diffusion coefficient value is projected horizontally onto the alkane line (AL), as shown with the dashed projection line (P). The intersection of this projection line P and the alkane line (AL) provides an estimated mean chain length ($N_{est}$) of approximately 8. This $N_{est}$ value is comparable with the mean chain length of 6.4 found from using Equation (4) and the full diffusion distribution.

Crude oils can contain asphaltenes that can affect the relaxation times (e.g., by reducing those times) in a mixture, while having only a minimal effect on the diffusion coefficients of that mixture. FIG. 7 shows an example D-$T_2$ map of a reservoir of oil that contains both dissolved gas and some asphaltene. In the example of FIG. 7, the NMR data was obtained in a laboratory at a simulated reservoir temperature and pressure of 83° C. and 6000 psi. In this case, the NMR signal lies to the left of the alkane line (AL), due to both the dissolved methane and to the small amount of asphaltenes in the mixture. The diffusion coefficient can still be used to determine the mean chain length, as in the example described with respect to FIG. 6. As shown in FIG. 7, the peak of the diffusion distribution is at approximately N=10, while the mean diffusion coefficient is approximately at N=12, so $N_{est}$12. As compared to a value of N=9.8 found from the GC, and N=9.6 found using Equation (4) and the full diffusion distribution, the $N_{est}$ of 12 provides an approximation of mean chain length with approximately a 20% deviation.

Figure 8:
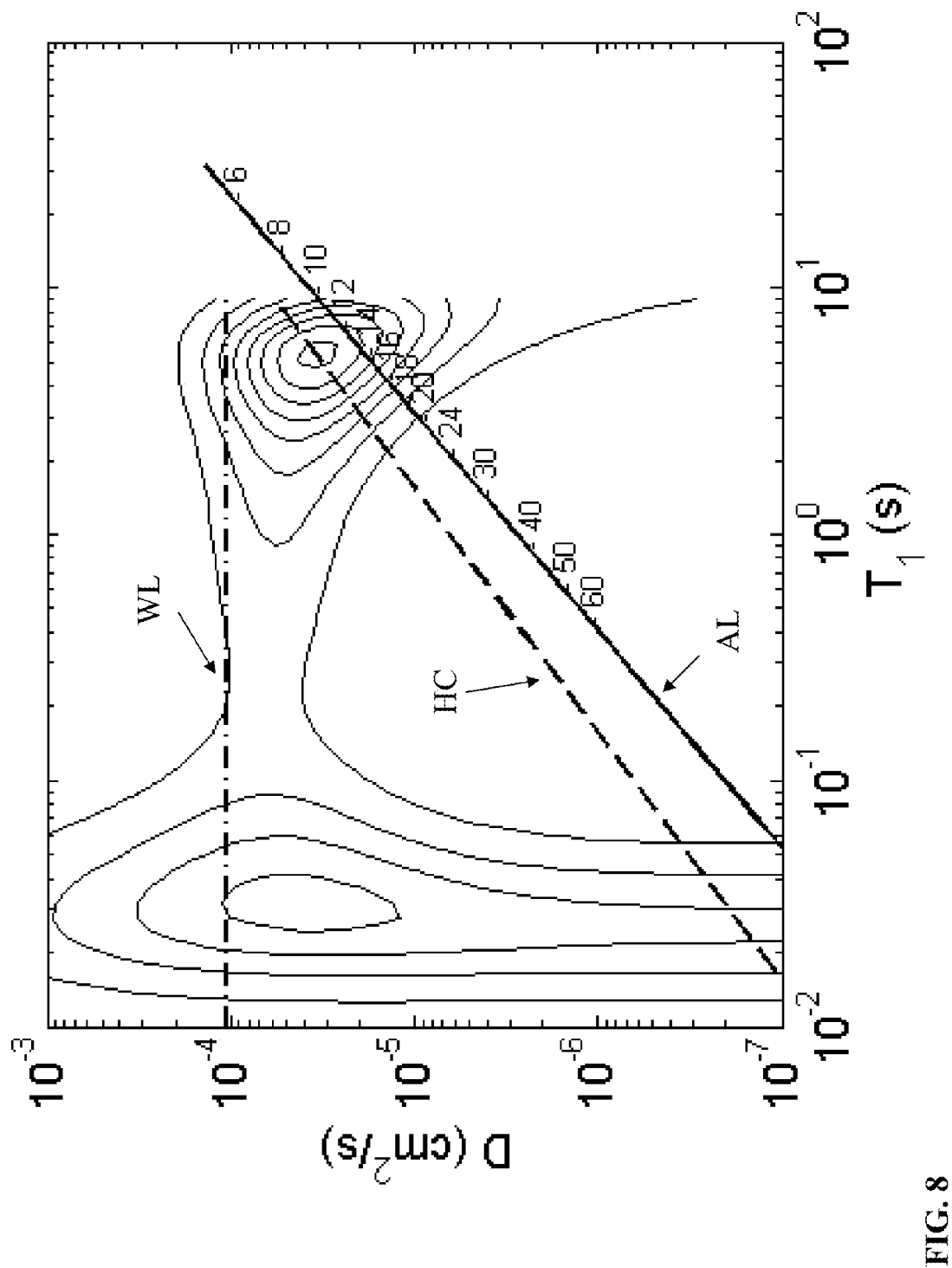

FIG. 8 illustrates an example of a D-$T_1$ map plotted from log data, including a mean chain length scale plotted along the alkane line (AL) according to embodiments of the invention. This example of oil was taken at T=143° C. and P=4000 psi. The signal centered around $T_1$=2 seconds (s) is the signal from the native oil, which could be mixed with oil-based drilling mud, and the signal at about $T_1$=$4 \times 10^{-2}$ s indicates bound fluid. In this case, the oil signal is well above (left of) the alkane line (AL). This can be due to one or more of the following: a) presence of dissolved gas, b) diffusion in a gradient affecting $T_2$ (which is partially corrected for in this case), c) the pulse sequence and wait times not being long enough to measure the full value of $T_2$, d) tool motion effects, or other factors, such as dissolved oxygen in the oil-based mud or surface relaxation where the oil is wetting a surface of the rock. In this example of FIG. 7, the inventors have discovered that the diffusion coefficients can be utilized to obtain a mean chain length of the mixture. The average diffusion coefficient is approximately at N=10, so according to embodiments, the estimate mean chain length is $N_{est} \approx 10$. The mean chain length calculated from Equation (4) using the full diffusion distribution of the oil in this case is N=7. This means that the $N_{est}$ is an accurate estimate of the actual mean chain length (e.g., within approximately 20-30% deviation from the calculated mean chain length N). It should be noted that, in this particular case, the mean chain length of the oil is estimated without first having to separate the oil signal from the bound fluid signal.

As evidenced by the examples in FIGS. 2-8, and according to various embodiments of the invention, even though $T_1$ and $T_2$ may be shortened by one or more of the above-noted effects, the diffusion coefficients of a substance (either in-situ or under simulated in-situ conditions) can still provide accurate estimates of the mean chain length of that substance. As described according to various aspects of the invention, the diffusion distributions can be used to obtain mean chain lengths, as long as the relaxation times are of a sufficient length such that a significant portion of the signal is not lost during the diffusion wait times in the NMR measurements. This relaxation time, e.g., for an oil, can be approximately equal to or greater than a 10-15 milliseconds. Additionally, in the case of restricted diffusion between composites within the substance (e.g., oil), the diffusion coefficients can be reduced. This reduction in the diffusion coefficient (e.g., on a D-$T_1$ or D-$T_2$ map) moves the diffusion distribution below the alkane line (AL). In some embodiments of the invention, the diffusion distributions provide reliable estimates for the mean chain length of a substance. Additionally, according to various embodiments, the position of the diffusion distribution compared to the alkane line can be used to determine other properties such as restricted diffusion, wetting, asphaltene presence, etc., of the substance (e.g., fluid, rock matrix) or environmental/experimental conditions.

In yet another group of embodiments of the invention, a method includes providing a mean chain length scale on an NMR map, where at least one of the x-axis, y-axis, or a diffusion/relaxation distribution is rescaled to increase the accuracy of particular estimating techniques. As noted with respect to the scales and estimates shown and described with reference to examples in FIGS. 2-8, a substantial portion of the $N_{est}$ values varied from their corresponding calculated N values by 2 or more (where N values were calculated from Equation (4) and the full diffusion distribution). As in the case of estimating the viscosity of a substance, reading off the mean values of the diffusion coefficient and relaxation times of a substance, in some cases, relies upon visual inspection of a plot (e.g., 1D and/or 2D NMR map). However, for viscosity, mean log relaxation times, or exp(log($T_2$)) are estimated. For those log distributions shown in the 1D and 2D NMR maps, the mean log relaxation times or diffusion coefficients can be easier to estimate as described with reference to FIGS. 2-8. However, for the mean chain length, $D_{ave} = \langle D^{1/v} \rangle^v$ and $T_{ave} \rangle T_{1,2}^{1/k} \rangle^k$. These can be larger than exp $\langle \log(D) \langle$ and exp⟩log($T_{1,2}$)⟩, respectively. Thus, the inventors have discovered that by estimating the mean diffusion coefficients and relaxation times from the 1D and 2D NMR maps, it is possible to underestimate $D_{ave}$ and $T_{ave}$ and, as a result, overestimate the mean chain length. This was partially illustrated in the various examples outlined in FIGS. 2-8 and their accompanying descriptions.

The inventors have discovered various methods to correct for this over-estimation. One embodiment includes an additional process of subtracting an overestimating constant, e.g., a value two (2) from the value of $N_{est}$ found from the methods outlined with respect to FIGS. 2-8.

In another embodiment of the invention, the x-axis, y-axis or the diffusion/relaxation distribution (i.e., the z-axis) can be rescaled to enhance estimation of $\langle D^{1/\nu}\rangle^\nu$ and $\rangle T_{1,2}^{1/k}\rangle^k$. For example, instead of plotting the log diffusion/relaxation distribution, one method according to aspects of the invention includes plotting the diffusion/relaxation distribution as a function of $D^{1/\nu}$ or $T_{1,2}^{1/k}$. Because the diffusion coefficients and relaxation times found on an NMR log can cover many orders of magnitude, and because practitioners in the art are accustomed to recognizing the positions of the oil and water signals on 2D maps plotted on a logarithmic scale, the inventors have discovered that it can be more beneficial to rescale the diffusion/relaxation distribution itself. One example method of rescaling the diffusion/relaxation distribution follows herein, but it will be understood that a variety of alternative methods are also possible within the spirit of the invention. When visually examining the distribution f(x), one can estimate the mean value of x, given by Equation (13):

$$\bar{x} = \int x f(x) dx.$$

This means that on a plot of f(x) versus x, it is advantageous to identify the center of mass, x=x̄. If a fulcrum were put at the point (x̄, 0), then the distribution f(x) would exactly balance at this point. Often, the median value of x is used to estimate the mean, where the median value is defined by the x satisfying Equation (14):

$$\int_{-\infty}^{\bar{x}} f(x) dx = \int_{\bar{x}}^{\infty} f(x) dx.$$

The median of x defines the point at which half of the weight of the distribution is above x and half is below x. While this approach can be beneficial in estimating the mean of a symmetric distribution (where substantially half of the distribution is above the mean, and half below), as the distribution becomes less symmetric, these estimates of x can become less reliable.

As mentioned herein, the difficulty in estimating D, for example, is because the process involves looking at a distribution on a log scale, so x=log D, and the mean estimate is x̄ = ⟨log D⟩.

In various aspects of the invention, a method includes multiplying a distribution f(x) by some power of D so that the mean value on the x scale reflects the correct mean of D. In particular, this process is illustrated in Equation (15):

$$\langle D^{1/\nu}\rangle = \int D^{1/\nu} f(\log D) d \log D]^\nu.$$

If the distribution f(log D) is rescaled by $D^\lambda$, the distribution g(log D)=$ND^\lambda$f(log D) is the result, where N is the normalization factor which ensures that ∫g(log D)d log D=1. Next, the process includes estimating the mean value of log D with respect to this new distribution, which is denoted by log D*. It is desirable to determine a λ value so that the mean of log D provides a D* value equal to $D_{ave}$ (or the value on the left-side of Equation (15)). Therefore, it can be desirable to find a λ value according to Equation (16):

$$\log D^* = \nu \log \langle D^{1/\nu}\rangle.$$

In general, there may not be a value of λ which will always satisfy exact equality in Equation (16). However, as noted herein, the method is more closely focused on approximating the right-hand side of Equation (16). When the left-hand side of Equation (16) is approximately equal to the right-hand side of that equation for a range of distributions, then the equation can be used in approximating a moment of the diffusion coefficient distribution. This moment of the diffusion coefficient distribution can be used to approximate the mean chain length of the substance. As the diffusion/relaxation distributions are often close to Gaussian or not much different from a Gaussian, aspects of the invention include initially using a Gaussian distribution, and solving for a value of λ that satisfies Equation (16).

In the case of a Gaussian distribution, Equation (17) applies:

$$f(x) = f(\log D) = \sqrt{\frac{\pi}{a}} e^{-a(x-c)^2},$$

Then, multiplying by $D^\lambda$ yields the following distribution in Equation (18):

$$g(\log D) = ND^\lambda f(\log D).$$

Letting x=log D, and substituting in the expression for f(x) from Equation (17), yields the following in equation (19):

$$g(x) = N\sqrt{\frac{\pi}{a}} e^{\lambda x} e^{-a(x-c)^2}.$$

Where a represents the width of the Gaussian distribution, and c represents the center of the Gaussian distribution. Completing the square in the exponent yields Equation (20):

$$g(x) = Ne^{-a\left(x-\left(c+\frac{\lambda}{2a}\right)\right)^2} e^{a\left(\frac{c\lambda}{a}+\frac{\lambda^2}{4a^2}\right)}.$$

The mean x for this distribution is x=c+λ/(2a), which yields an average with respect to g(x), as represented in Equation (21):

$$\langle \log D\rangle = c + \frac{\lambda}{2a} = \log D^*.$$

Next, for the Gaussian distribution f(log D) given above, the mean value of $D^{1/\nu}$ is provided in Equation (22):

$$\langle D^{1/\nu}\rangle = \int D^{1/\nu} f(\log D) d \log D.$$

Again, letting x=log D, and substituting the expression for f(x) in Equation (17) yields Equation (23):

$$\langle D^{1/\nu}\rangle = \sqrt{\frac{\pi}{a}} \int e^{x/\nu} e^{-a(x-c)^2} dx.$$

Performing the integral by completing the square in the exponent yields Equation (24):

$$\langle D^{1/\nu} \rangle = e^{\left(\frac{c}{\nu} + \frac{1}{4a\nu^2}\right)}.$$

Raising this expression to the $\nu^{th}$ power and taking the log yields Equation (25):

$$\nu \log \langle D^{1/\nu} \rangle = c + \frac{1}{4a\nu}.$$

According to Equation (16), it is desirable to set Equation (25) equal to the equation for log D* in Equation 21, which yields Equation (26):

$$c + \frac{\lambda}{2a} = c + \frac{1}{4a\nu}.$$

Solving for $\lambda$ yields Equation (27): $\lambda = \frac{1}{2}\nu$.

Thus, for Gaussian distributions, multiplying by $D^{1/(2\nu)}$ can shift the mean value of the distribution to the desired value, regardless of the value of a (Gaussian distribution width) or c (Gaussian distribution center point).

Multiplying the distribution by $D^{1/(2\nu)}$ also gives an estimate of the mean chain length for the diffusion distributions considered herein. Rescaling helps to improve the estimate for $D_{ave}$ so that the estimated mean chain length will substantially match that mean chain length calculated from the full distribution using Equation (4).

FIGS. 9-15 provide examples of NMR maps corresponding to the NMR maps of FIGS. 2-8. The NMR maps of FIGS. 9-15 are rescaled relative to those of FIGS. 2-8, and in particular, the intensity at each point along the plots (NMR maps) has been multiplied by $D^{1/(2\nu)}$ in these rescaled cases.

Figure 9:
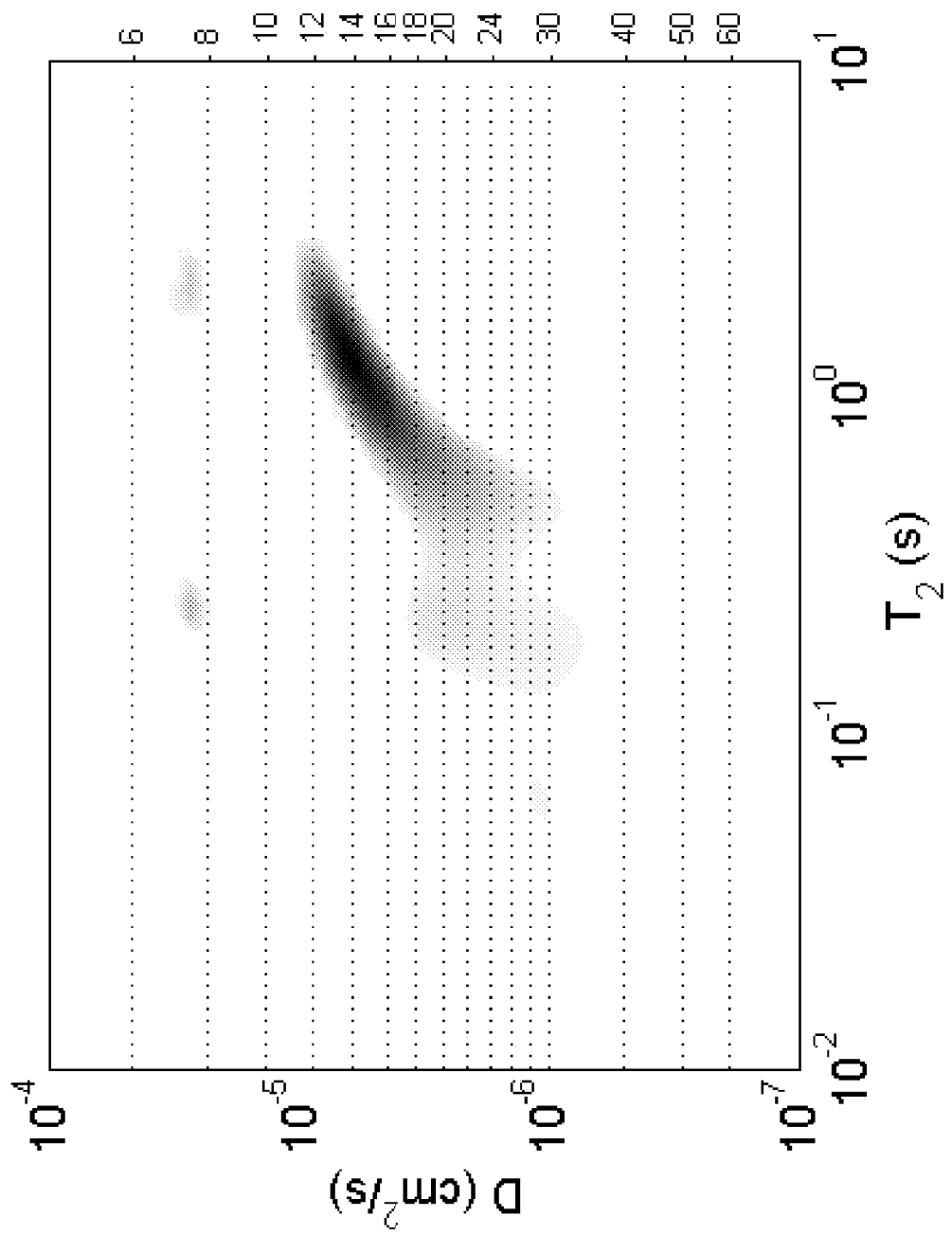
FIGS. 9-15 show example NMR maps illustrating various rescaling features according to embodiments of the disclosure.
Figure 10:
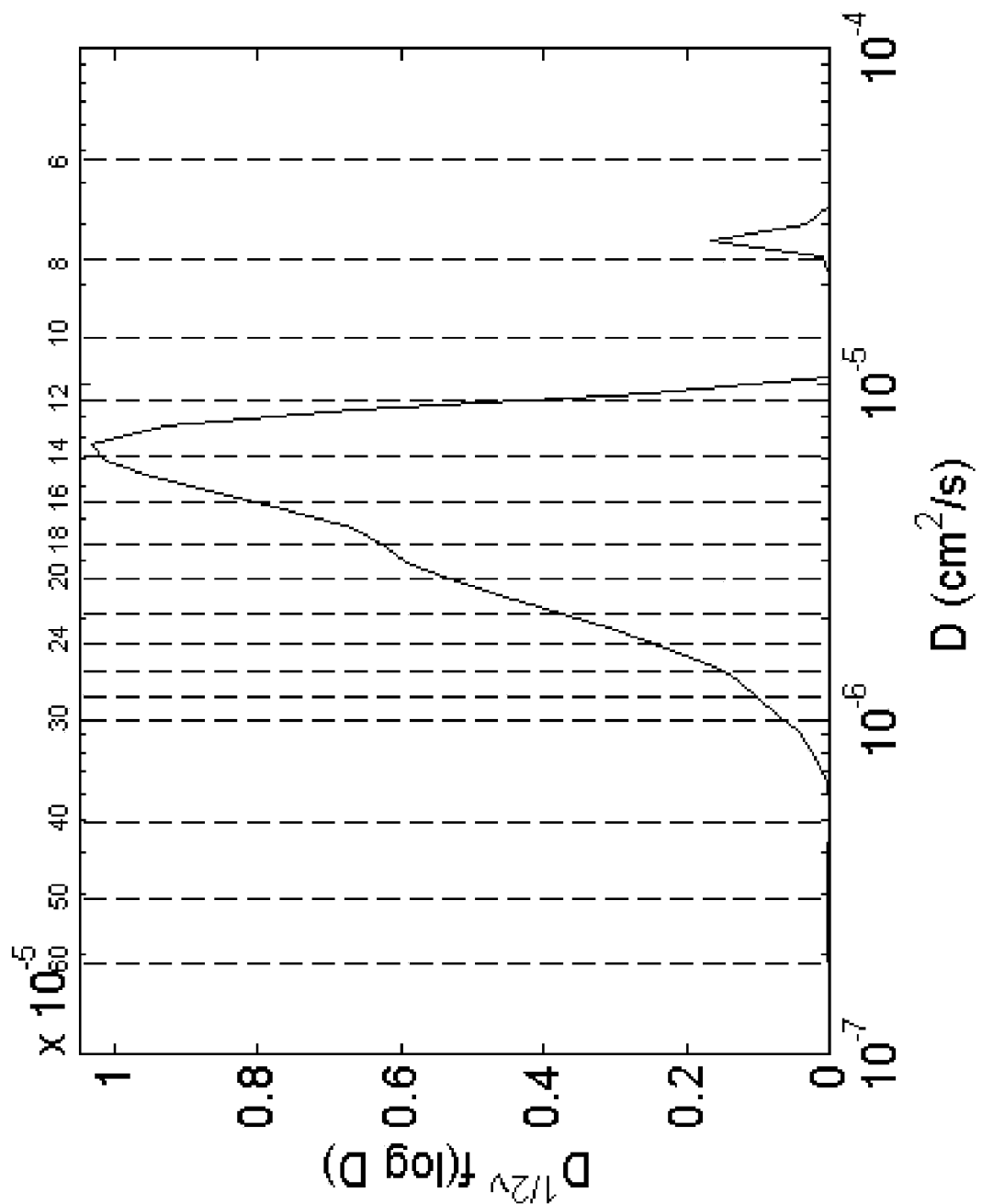

Turning to FIG. 9, a D-$T_2$ map illustrating a rescaled 2D distribution is shown according to aspects of the invention. This D-$T_2$ map is derived from the same data plotted in FIG. 2 of the dead oil high in saturates. The rescaled 2D distribution is shown in FIG. 9, and the rescaled diffusion distribution is plotted in FIG. 10. As shown in FIG. 10, the peak of the oil diffusion distribution is located at approximately N=14, and after accounting for the upward adjustment described with respect to various embodiments, the estimated mean chain length $N_{est}$ is approximately 15 or 16. This substantially matches the value of N=16 found using Equation (4).

Figure 11:
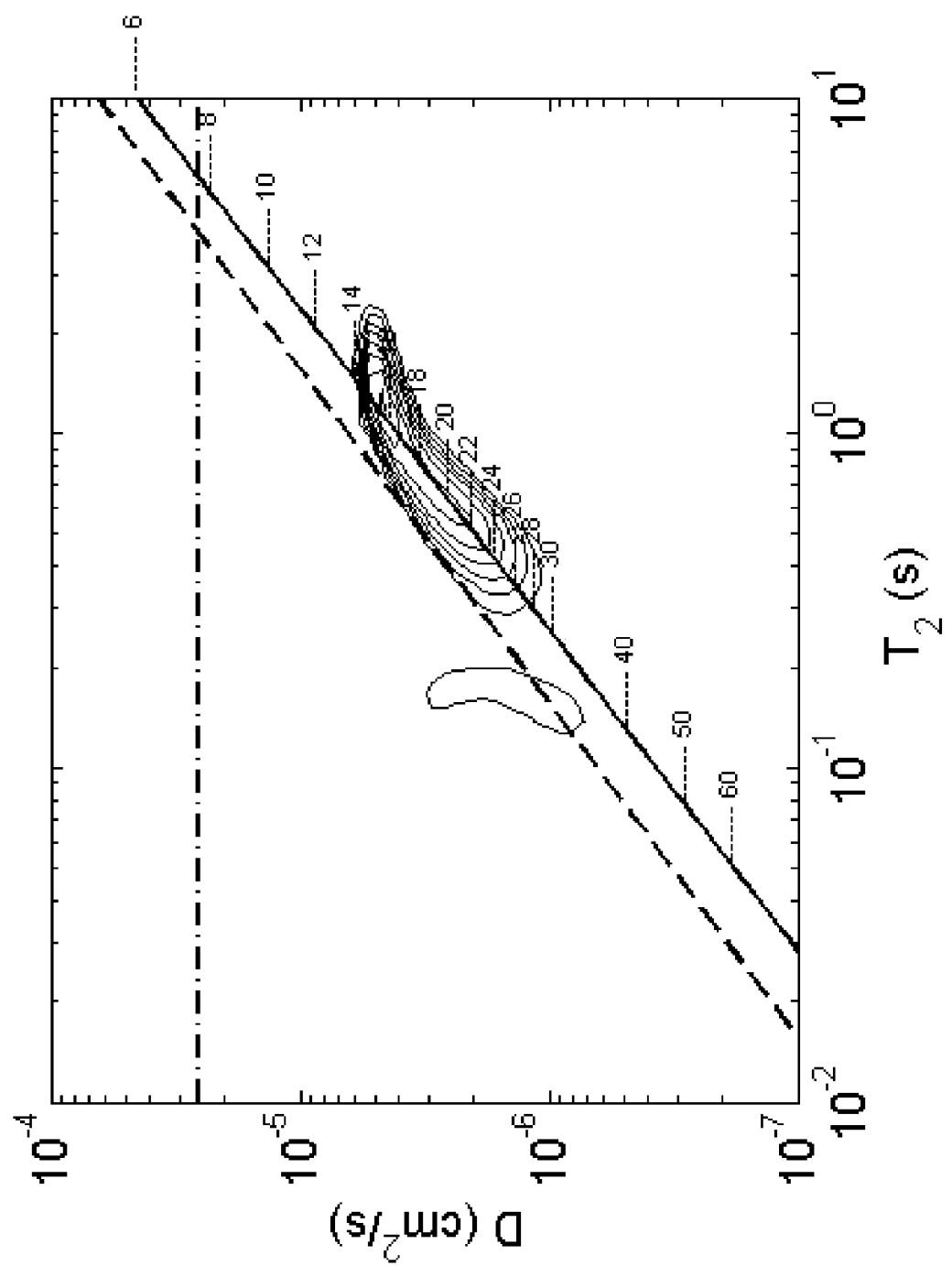
Figure 12:
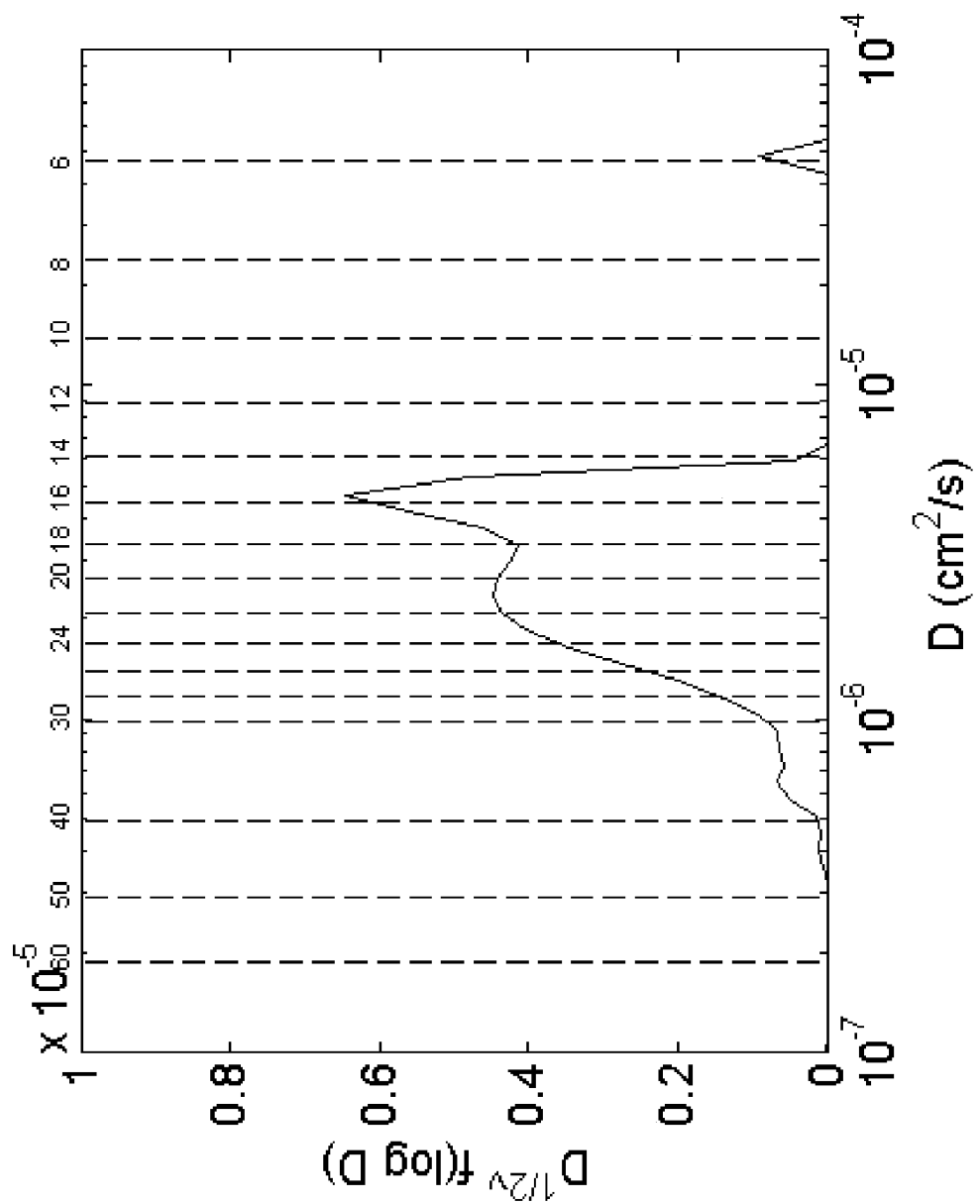

A rescaled D-$T_2$ map for the second example (corresponding to FIG. 5) including another dead oil with somewhat higher aromatic content than the example of FIG. 9, is plotted in FIG. 11. The peak of the distribution relative to FIG. 5 is shifted downward to N=16, and $N_{est}$ is approximately 19. The diffusion distribution for this oil is plotted in FIG. 12. It may be simpler to make a quantitative estimate from this 1D plot in FIG. 12 as compared with the 2D plot in FIG. 11, because the y-axis in FIG. 12 more clearly illustrates the weight of the distribution. In this case, $N_{est}$ is approximately equal to 20, which again substantially matches the value found using Equation (4) and described with respect to FIG. 5.

Figure 13:
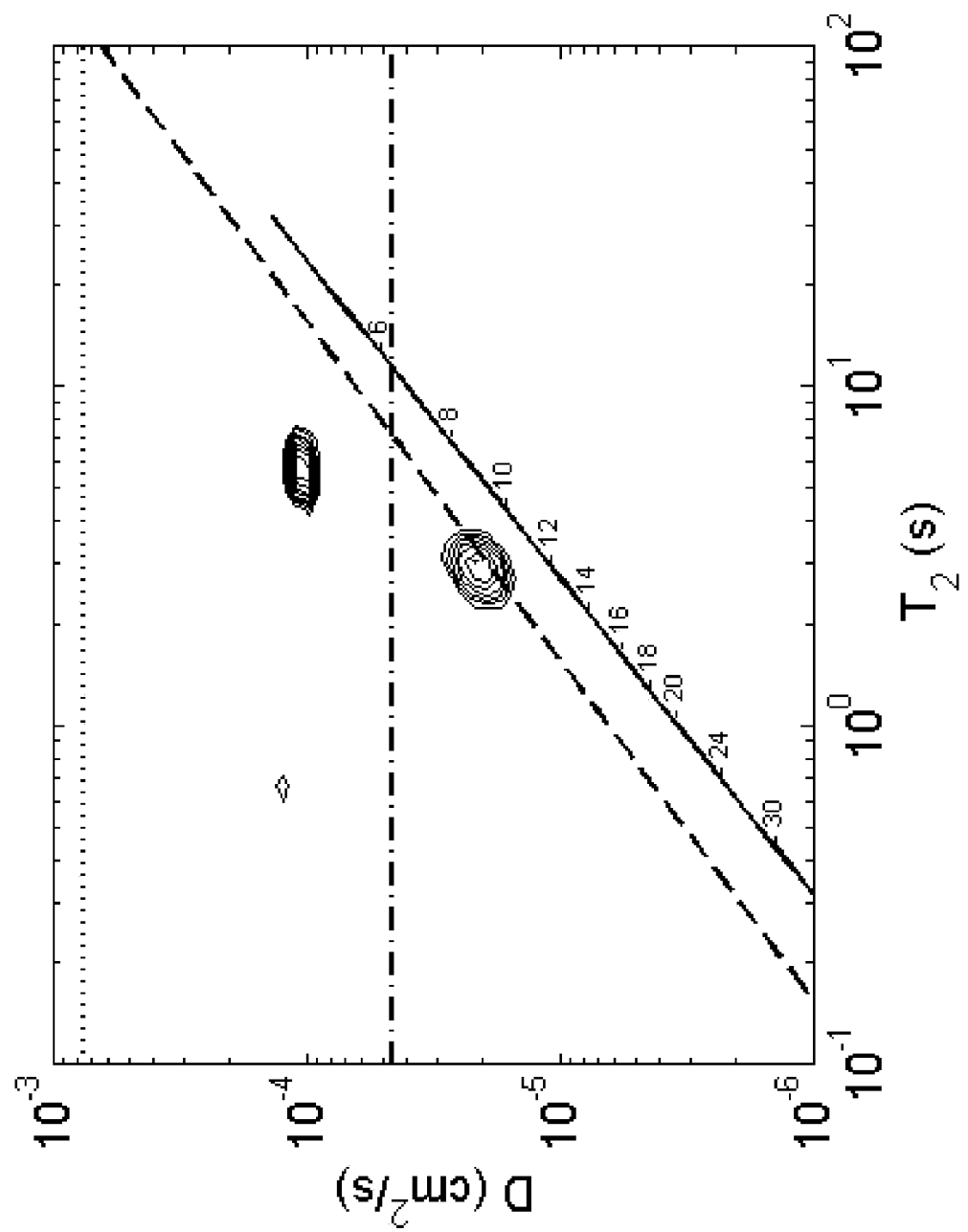
Figure 14:
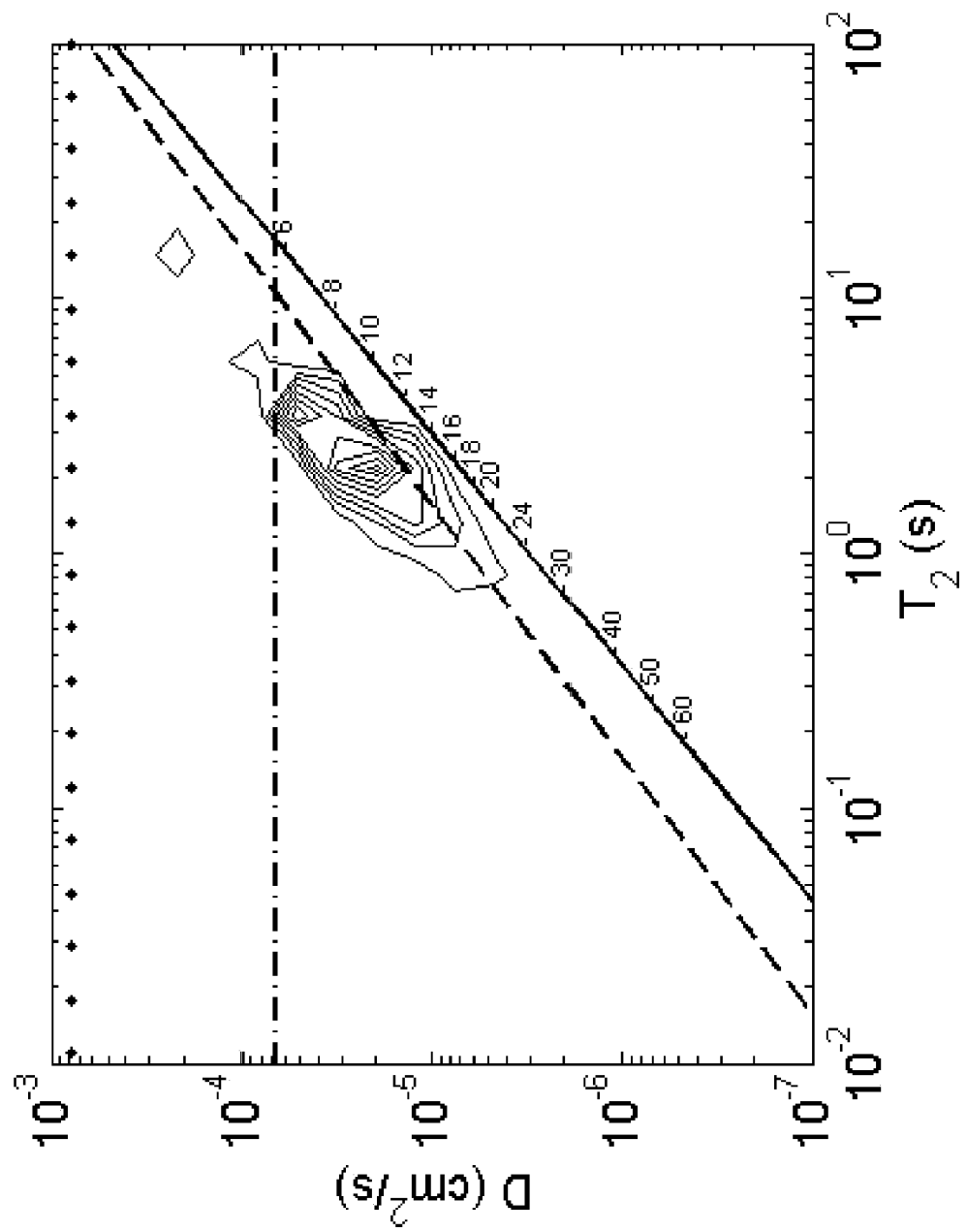
Figure 15:
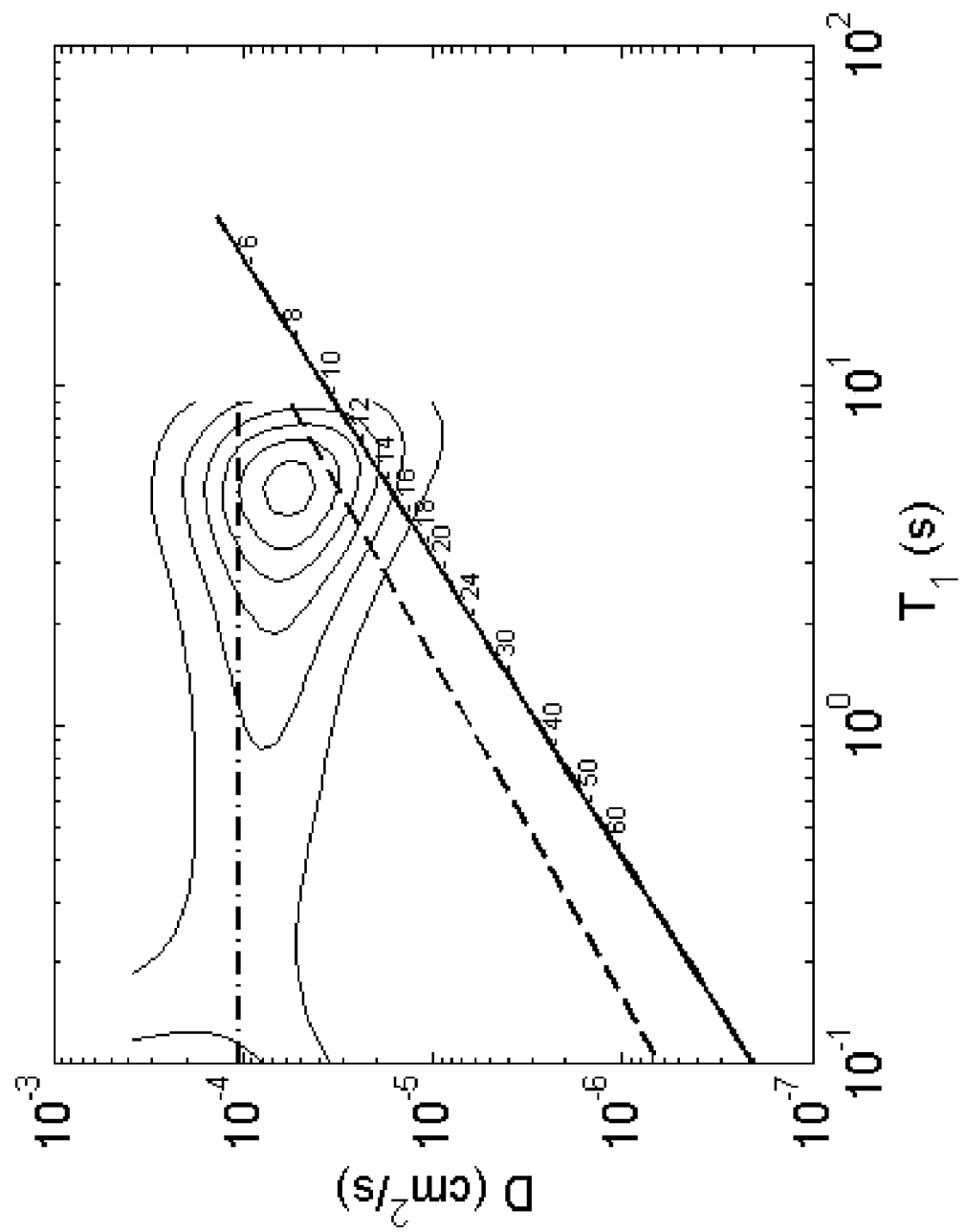

FIGS. 13-15 illustrate rescaled 2D NMR maps (D-$T_2$, D-$T_2$ and D-respectively) of live oils, which include mean chain length scales plotted according to embodiments of the invention. The data used to construct these 2D NMR maps is substantially similar to the data used in constructing the NMR maps of FIGS. 6-8. Various embodiments of the invention include examining each scaled 2D map, and using the diffusion distribution to determine a value of $N_{est}$. In particular, the D-$T_2$ map for the mixture of methane and hexadecane is plotted in FIG. 13. After performing the rescaling according to embodiments, the height of the methane peak has been enhanced, and $N_{est}$ is shown between 6 and 7. The D-$T_2$ map for the reservoir oil is shown in FIG. 14. In this case, $N_{est}$ is approximately between 9 and 10. Lastly, the D-$T_1$ map from the NMR log data is given in FIG. 15, and $N_{est}$ is approximately equal to or slightly greater than 7. In all three cases illustrated in FIGS. 13-15, the rescaled $N_{est}$ more closely agree with the values of N calculated from the full diffusion distributions as compared with the examples noted with reference to FIGS. 6-8.

As noted with respect to the examples above, various embodiments of the invention include a method for plotting a scale on 1D or 2D NMR maps about a substance, including diffusion distributions, relaxation time distributions, D-$T_2$ maps and $T_1$-$T_2$ maps. These maps and scales can be used for estimating the mean chain length or molecular size of the molecules in the substance. Additionally, the scales shown and described with respect to various aspects of the invention make it possible to estimate mean chain lengths of a substance (e.g., oil) from 2D maps, where the substance includes multiple fluids (e.g., both oil and other fluids) without requiring one to separate out the primary (e.g., oil) signal first.

In other embodiments of the invention, a method includes determining a molecular size (e.g., a mean chain-length a chain length distribution, a binned molecular size distribution, a hydrodynamic radius and/or a hydrocarbon number) of a substance (e.g., crude oil) based upon nuclear magnetic resonance (NMR) signals (e.g., those obtained in situ). The method can further include generating a plot of the molecular size of the substance as a function of a sampling parameter of that substance. In various embodiments, the sampling parameter includes a depth of the substance, e.g., a depth of the substance in situ. In various other embodiments, the sampling parameter can include a time at which the NMR signals were obtained (e.g., in a time logged sample process), or a sample batch identifier of the substance. For example, in the case that the NMR data is obtained from the substance in a chemical plant, a lab core analysis, or another similar analysis, the plot can include data about a molecular size of the substance as any function of the analysis performed. This could include generating a plot of the molecular size of the substance as a function of a time at which it was analyzed. Where a substance is analyzed on a conveyor belt or in a pipe, e.g., in batches or groups, the plot could also indicate the molecular size of the substance as a function of its sample batch identifier or a time at which the sample batch was analyzed. The method can further include providing the plot for display (e.g., at a user interface or other interface).

In some cases, as described with other embodiments of the invention, determining the molecular size of the substance can include calculating the molecular size (e.g., mean chain length) from at least one of a diffusion measurement D or a relaxation measurement $T_1$, $T_2$ of the substance from the NMR signals. Specific embodiments include determining a fluid volume within the substance from the at least one of the diffusion measurement or the relaxation measurement. In this case, an intensity of the plot can be varied based upon the fluid volumes (relative or absolute) within the substance.

Various embodiments include isolating sub-signals within the NMR signals to obtain data about portions of the substance e.g., an oil within the substance, a gas within the substance or an oil-based mud within the substance. In some cases, methods include determining a molecular size (e.g., mean chain-length) of at least one of: the oil, the gas or the oil-based mud at each of a plurality of depths in-situ. This allows for plotting of the mean chain length at each of the respective depths. The NMR signals can be separated prior to determining the mean chain lengths in some cases. As described with respect to various other embodiments, the NMR sub-signals can be separated using an NMR map. It is further understood that according to various embodiments of the invention, the methods described herein could be applied to raw NMR data, exclusive of a map or plot as shown herein.

In some cases, the mean chain length of a substance and the chain lengths in a distribution can be found from known diffusion distributions or relaxation distributions. For example, if the diffusion distribution is defined by $f(D_i)$, where $f(D_i)$ is the number of protons with diffusion coefficient $D_i$, then the mean chain length N and the chain lengths in the distribution $N_i$ can be defined by Equations (28) and (29):

$$\overline{N} = A^{\frac{1}{\nu+\beta}} \left( \frac{\sum_i f(D_i) \Delta D_i}{\sum_i f(D_i) D_i^{1/\nu} \Delta D_i} \right)^{\frac{\nu}{\nu+\beta}},$$

and $$N_i = \left( \frac{A}{D_i \overline{N}^\beta} \right)^{\frac{1}{\nu}}.$$

Similarly, the mean chain length and the chain lengths in the distribution can be determined using the relaxation times. For example, the mean chain length calculated from $T_2$ can be defined by Equation (30):

$$\overline{N}_{T_2} = \frac{1}{B^{\kappa+\gamma}} \left( \frac{\sum_i f(T_{2i}) \Delta T_{2i}}{\sum_i f(T_{2i}) T_{2i}^{1/\kappa} \Delta T_{2i}} \right)^{\frac{\kappa}{\kappa+\gamma}},$$

where now $f(T_2)$ is the number of protons with relaxation time $T_2$. These above-noted equations can be modified to account for a scenario in which the mean chain length is shorter, e.g., of nominal length.

Figure 16:
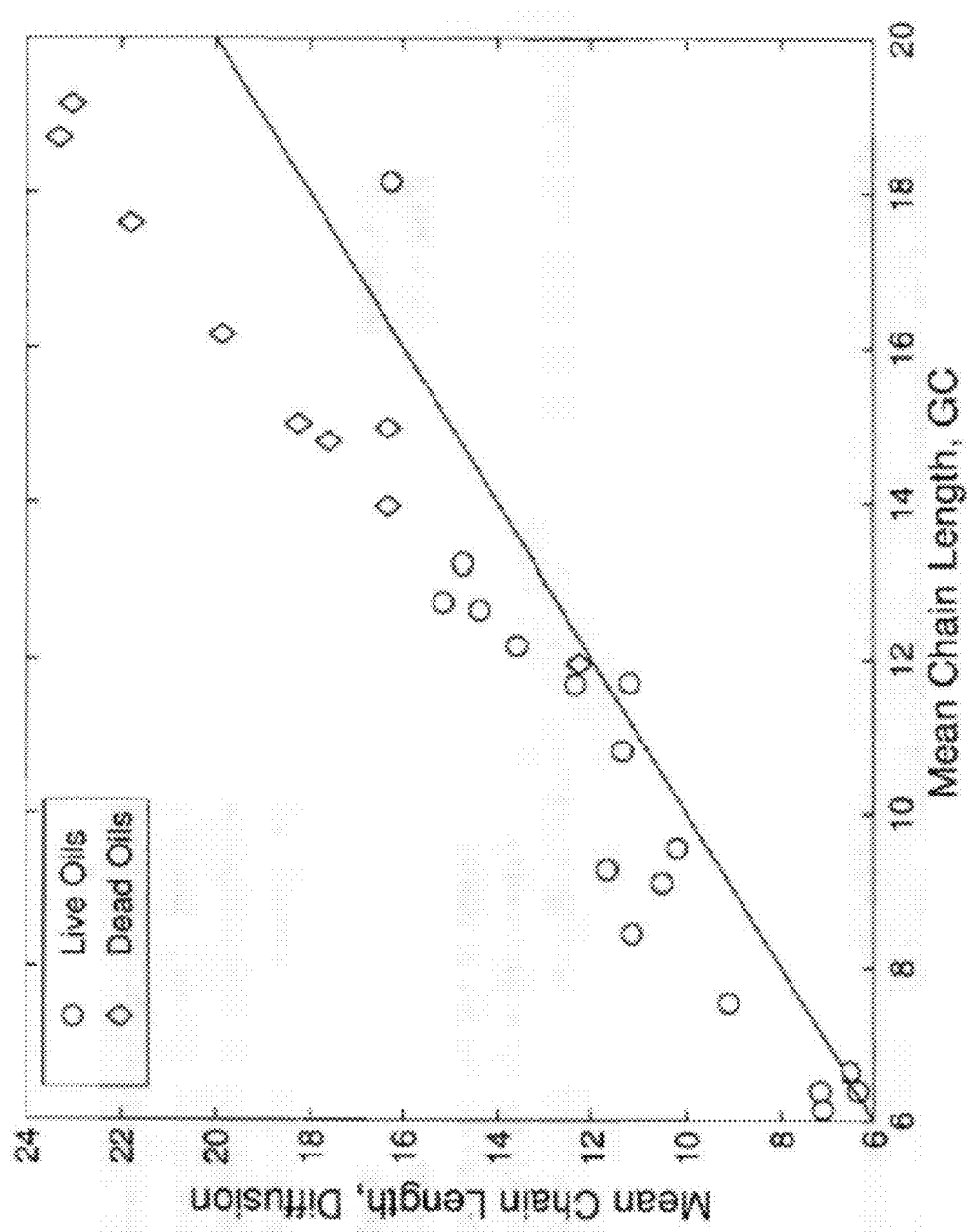
FIGS. 16-18 show example NMR maps illustrating various features according to embodiments of the disclosure.

FIG. 16 is an example graph showing a mean chain length of substances calculated from NMR diffusion versus the mean chain length of those substances calculated from a conventional gas chromatography (GC) approach. In this case, the substances include live oils and dead oils. The data for live oils are indicated by circular shapes, and the data for dead oils are indicated by diamond shapes. The N from the NMR diffusion calculations are substantially within about 20% of those calculated from the GC approach. This indicates that those NMR diffusion calculations are within an acceptable level of error when compared with the GC approach. In this example, the oils include both oils high in saturates and oils with asphaltene. In addition, the measurements on the live oils in this example used eight (8) gradient values and had relatively low signal-to-noise-ratio (SNR), so the live oil data approach that of desirable log data. Thus, in this example, the mean chain length calculated from the diffusion distribution is shown to be substantially reliable, as the diffusion distribution calculation is within approximately 20% of the conventional GC calculation.

In other embodiments of the invention, the width of the chain length distribution can be calculated to obtain a continuous log of the width of the distribution versus depth. In particular, the width, or second moment of the distribution of $\log(N_i)$ is directly related to the second moment of the log distribution of diffusion coefficients or relaxation times. For example, $\sigma^2_{ln(N)}$, the square of the width of the distribution of $\log(N_i)$, can be calculated from the distribution of the log of the diffusion coefficients, $f(\log(D))$, with Equation (31):

$$\sigma^2_{ln(N)} = \frac{1}{\nu^2} \left[ \frac{\int_{-\infty}^{\infty} [\log(D)]^2 f(\log(D)) d\log(D)}{\int_{-\infty}^{\infty} f(\log(D)) d\log(D)} - \left( \frac{\int_{-\infty}^{\infty} \log(D) f(\log(D)) d\log(D)}{\int_{-\infty}^{\infty} f(\log(D)) d\log(D)} \right)^2 \right].$$

This expression is independent of temperature and pressure, as the temperature and pressure dependence of the original NMR signal is eliminated. In some cases, the width of the chain length distribution is more sensitive to the SNR and choice of NMR apparatus than the mean chain length. Despite this sensitivity, for sufficiently high-quality log data, e.g., log data with high SNR, it is possible to obtain a depth log of the width of the distribution.

In various embodiments, in order to obtain a log of N versus depth, first the region where the oil, mud or gas is expected to occur is identified. This can be performed by specifying the minimum and maximum diffusion coefficients and relaxation times of the oil, gas or mud signal. Identification can also be performed by defining the desired regions on a 2D map via non-rectangular (e.g., random) shapes such as complex polygons or ovals. One method for identifying the boundaries of these shapes/regions is to examine the 2-D map as a function of depth, and observe in which regions the signal from these fluids lies. In some cases, the water and oil signal can overlap. In this case, the $T_2$ distribution of the oil signal can be determined using conventional approaches for determining the amount of oil and water for each $T_2$ value.

In other embodiments of the invention, a method can include making a preliminary assumption that each fluid lies within approximately the same region even as the depth in-situ is varied. At each depth in-situ, the signal from each region on a $D$-$T_1$ map can be isolated and projected onto the relaxation and diffusion axes to give the D distribution and the $T_1$ or $T_2$ distribution. In this case, Equations (28) and (30) could then be used to calculate N as a function of depth.

Figure 17:
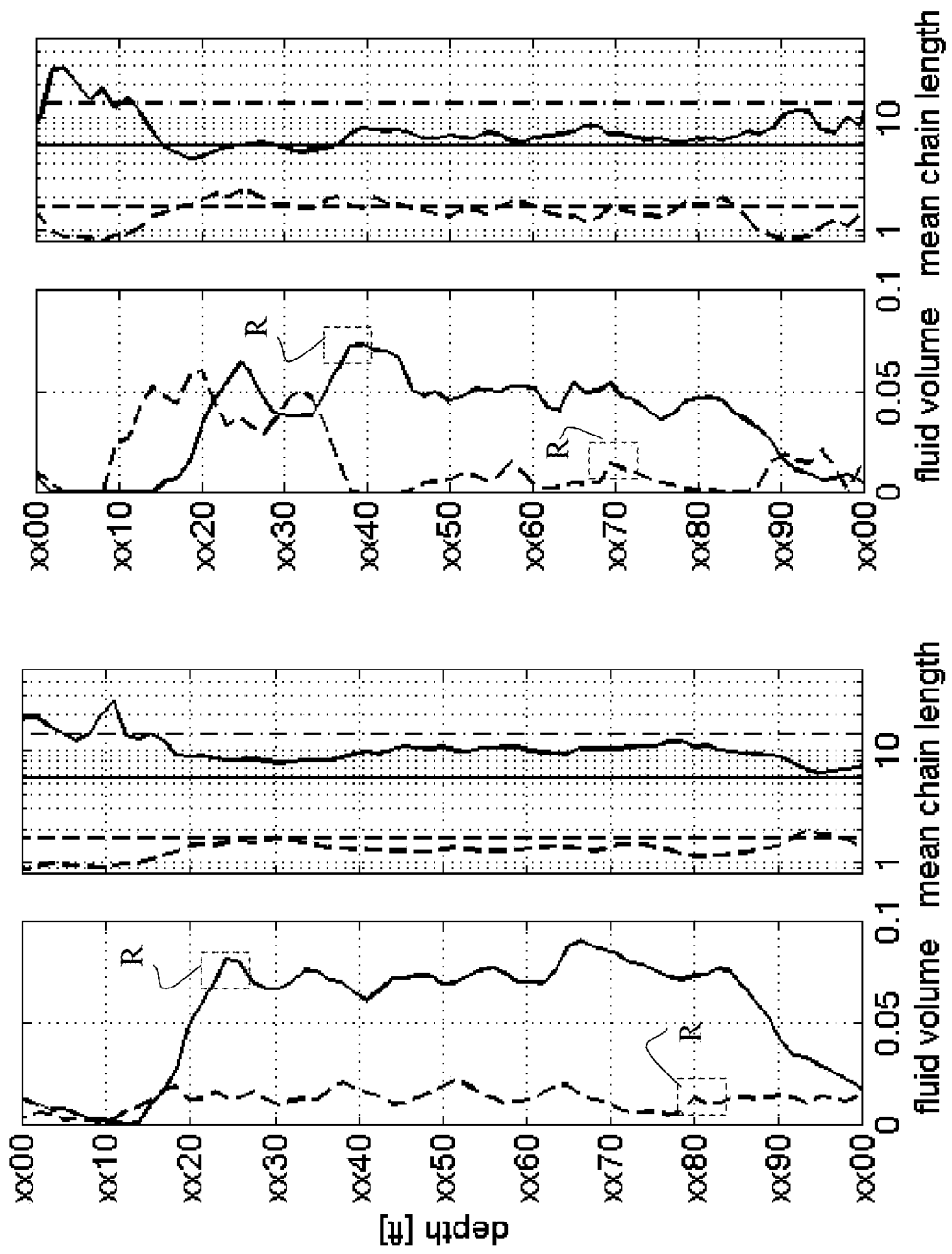

In FIG. 17, an example result of the above-noted calculations is plotted using diffusion distributions to obtain mean chain lengths. This data is plotted from example log data obtained in situ. The left-hand set of two panels display data obtained approximately 1.5 inches into a rock formation, and the right-hand set of two panels display data obtained approximately 4.0 inches into the rock formation. In each set, the first panel shows the total oil and gas fluid volumes, obtained by taking the area under the oil and gas diffusion distributions from a $D$-$T_1$ map. This may be substantially equivalent to measuring the total amplitude of an expected oil signal and the total amplitude of the gas (hydrocarbon) signal in a $D$-$T_1$ map. Thus, for the shallow shell (1.5 inches), an oil zone exists from about xx20 to xx90 ft, while for the deeper shell (4.0 inches), an oil zone exists from about xx25 to xx90 ft and gas from about xx10 to xx35 ft.

In FIG. 17, in each set of data, the second panel indicates a mean chain length for the gas and oil plotted as a function of depth in-situ. The mean chain lengths $N_D$ for the gas and oil calculated from the NMR diffusion measurement are shown by dashed and solid lines, respectively. The mean chain lengths calculated from GC, $N_{GC}$, are indicated by straight lines. As shown in FIG. 17, the $N_D$ for the oil lies almost entirely between the $N_{GC}$ lines for the native oil and the OBM. In the deeper shell (right-hand set of data), the $N_D$ is close to the $N_{GC}$ of the native oil, and in the shallower shell (left-hand set) the $N_D$ moves consistently closer to the $N_{GC}$ of the OBM as the depth increases.

This example further shows that in the region in the deeper shell where there is a transition from oil to gas, the $N_D$ from both the oil and gas show a gradient toward lower N as the depth decreases. This gradient could later be explored in more detail by NMR equipment such as a formation tester. In this example, the increase in $N_D$ for the oil near the top of the log depth can be ignored because there is only a nominal amount of oil in this region, which can make the calculation ill-defined. In order to avoid misinterpreting this type of situation, the data from the two panels for each shell can be combined into one figure.

Figure 18:
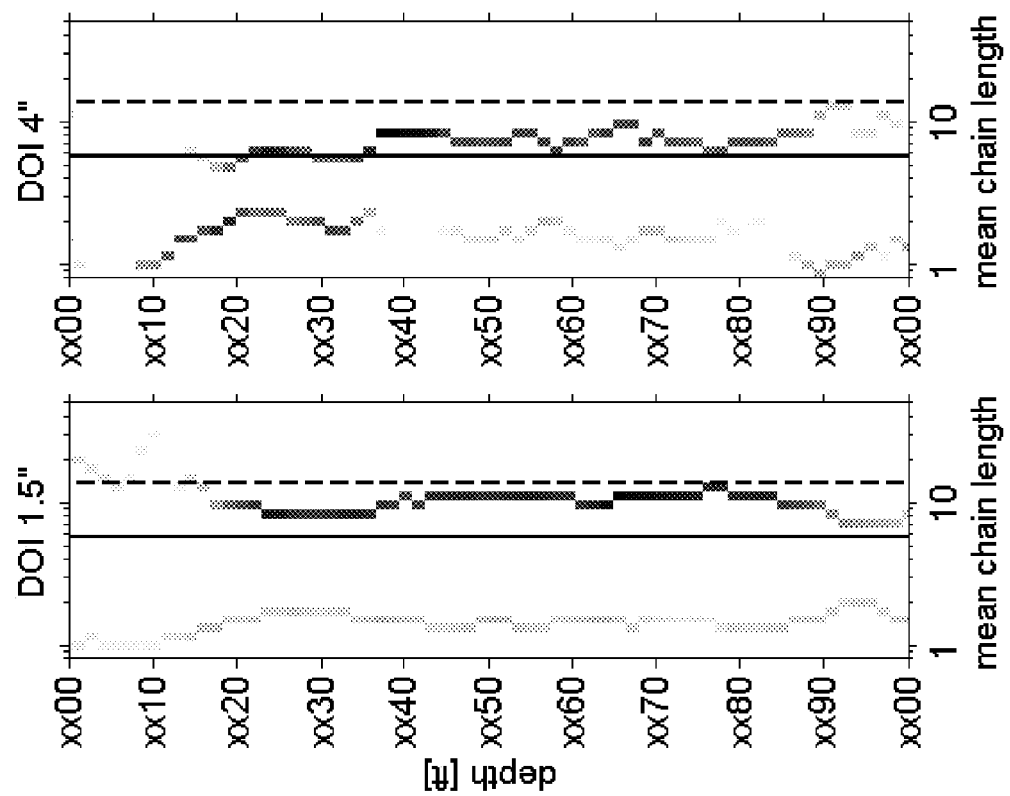

In FIG. 18, the mean chain length of a substance is plotted as a function of depth, with the intensity of the line varied according to the volume of the substance. In most cases, the GC of the oil is not known. Thus, in conventional logs, the vertical lines shown in FIGS. 17 and 18 for the native oil and gas signal would not necessarily be visible. As shown in FIGS. 17 and 18, the effects of invasion on the oil composition are quantifiable in graphical format. In addition, changes in the fluid composition, including both step changes and gradients, can be identified in the Figures. These changes in fluid composition can be used to determine if additional NMR exploration is desirable, including for example gathering more formation tester data points. In some cases, greater variation in the fluid usually indicates a desire to conduct more formation tester sampling. As described herein, the values of $N_D$ or $N_{T1,2}$ found from the NMR measurements can be compared directly with those found from the composition measurements of a downhole fluid analyzer (DFA).

In still other embodiments of the invention, a method includes obtaining nuclear magnetic resonance (NMR) signals about the substance, and calculating a molecular size (e.g., mean chain-length) of the substance based upon the NMR signals. The method further includes providing a one-dimensional (1D) nuclear magnetic resonance (NMR) log representing the calculated molecular size of the substance at a plurality of depths of the substance. In various embodiments of the invention, where the NMR signals about the substance are obtained in-situ, the 1D NMR log can represent the calculated molecular size of the substance at a plurality of depths of the substance in-situ. In various embodiments of the invention, the log can take a form substantially similar to the examples shown in FIGS. 17-18. In these cases, as shown in the example of FIG. 17, the 1D NMR log includes an actuatable region ("R") at each of the plurality of depths for providing at least one of a two-dimensional (2D) NMR map or a chain length distribution of the substance at the each of the plurality of depths.

In the case that the 2D NMR map is provided, the 2D NMR map can take the form of any 2D NMR map shown or described according to various aspects of the invention. In some cases, the actuatable region R can include an actuatable button, icon, or other indicator that can be actuated via a conventional user interface, e.g., using a pointer-mouse configuration, touch screen, keypad, etc. In some cases, actuating the region R at a selected depth can prompt display of the 2D NMR map of the substance, sometimes in another display screen, or sometimes within the same display screen. In some cases, the region R can be actuated by hovering a pointer or other indicator over the region, whereby a "preview" of the 2D NMR map is temporarily displayed overlying the log.

In other embodiments of the invention, the distribution of the molecular size or chain length can be calculated to obtain a continuous log of the distribution versus depth (or time, etc.). The chain length distribution can be obtained from the weight percent distribution of diffusion coefficients (Equation 6), and the relation between chain lengths and diffusion coefficients given in Equations 28 and 29. Similarly, the chain length distribution can be obtained from the weight percent distribution of relaxation times and the relation between chain lengths and relaxation times given in Equations 30 and 31. For example, Equation 6 gives the expression for the weight percent distribution of the diffusion coefficients $w(D_i)$. Equations 28 and 29 then provide a method for obtaining the chain length $N_i$ corresponding to the diffusion coefficient $D_i$. Using this relationship, it is possible to find w as a function of $N_i$. To obtain the chain length distribution, various embodiments of the invention include multiplying this function w(N) by the Jacobian which results from changing variables from $D_i$ to $N_i$. If the D, and $N_i$ are both measured on a log scale, then the Jacobian is $d \log D_i/d \log N_i = v$. The last equality comes from taking the derivative of Equation 29.

If, instead, the chain lengths are on a linear scale, this Jacobian is $d \log D_i/dN_i = v/N_i$. Thus, the weight percent distribution for the chain lengths is given by $W(N_i) = vw(N_i)$ for a log distribution and $W(N_i) = vw(N_i)/N_i$ for a linear distribution. For each value of depth, a 1-D plot of $W(N_i)$ versus $N_i$ can be displayed. In this manner, a 2-D plot is obtained which provides a continuous log of chain length distribution versus depth. Additionally, the chain length distributions may be further discretized into bins (as binned chain length distributions, or simply, "binned molecular size distributions") which may correspond to data obtained from instruments including spectroscopic tools which often present results as three numbers, including percent of methane (C1), percent of ethane through pentane (C2-5), and percent of hexane and higher (C6+). This binning involves summing the individual components ($N_i$) to form the chosen bins. This method increases the amount of total signal in each represented component at the cost of reducing the resolution of the distribution.

Figure 19:
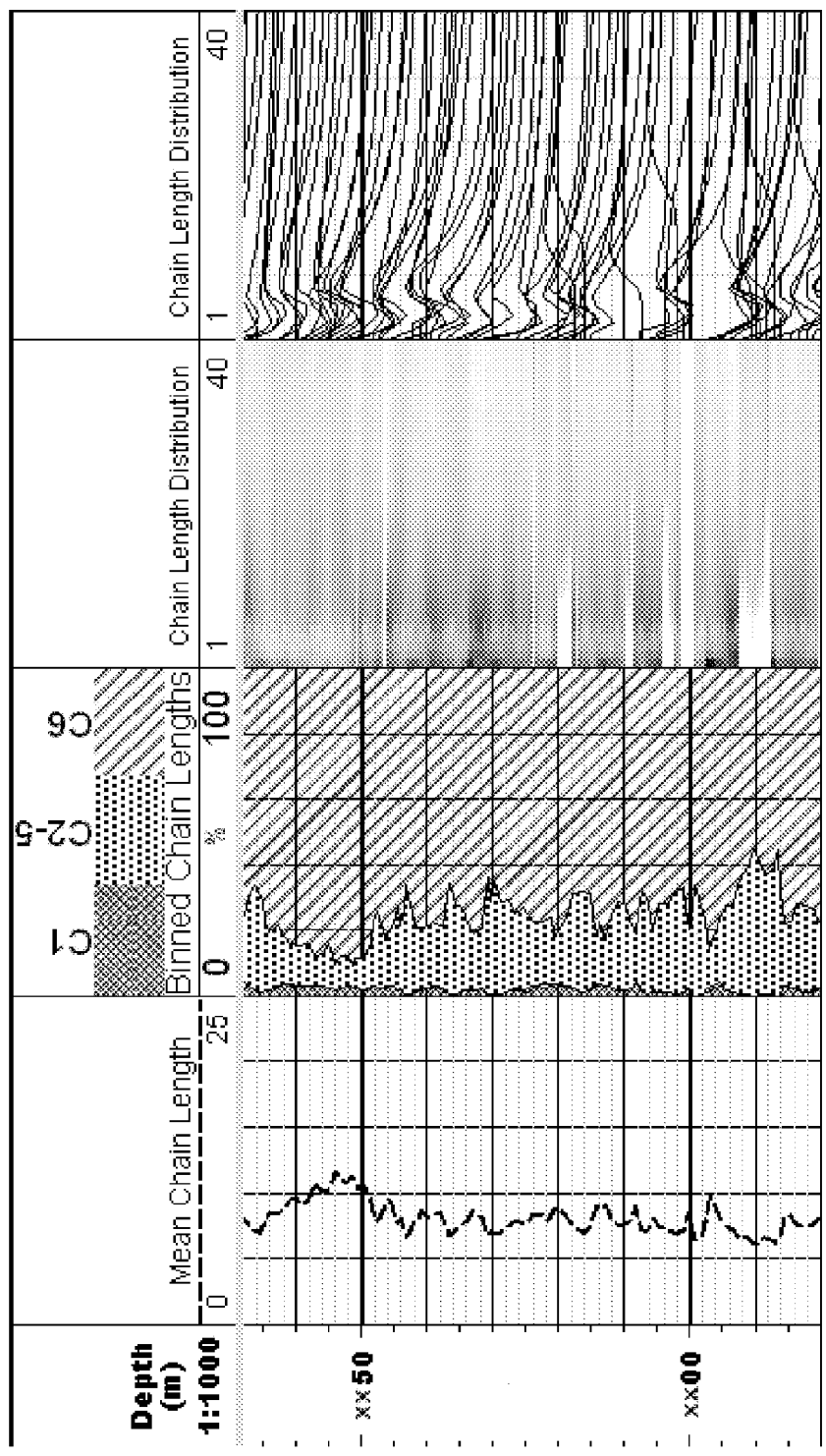
FIG. 19 shows an example chain length distribution plot illustrating various features according to embodiments of the disclosure.

Example 1-D chain length distribution plots are shown in FIG. 19. From left to right: the first plot shows the mean chain length; the second plot shows a possible embodiment of the discretization method of plotting the chain length distribution; the third plot illustrates a chain length distribution where darker shading indicates a higher concentration of a particular chain length; and the fourth plot shows a depth-by-depth plot of the distribution of the third plot, where each curve is offset to correspond to the depth at which the measurement was obtained.

Figure 20:
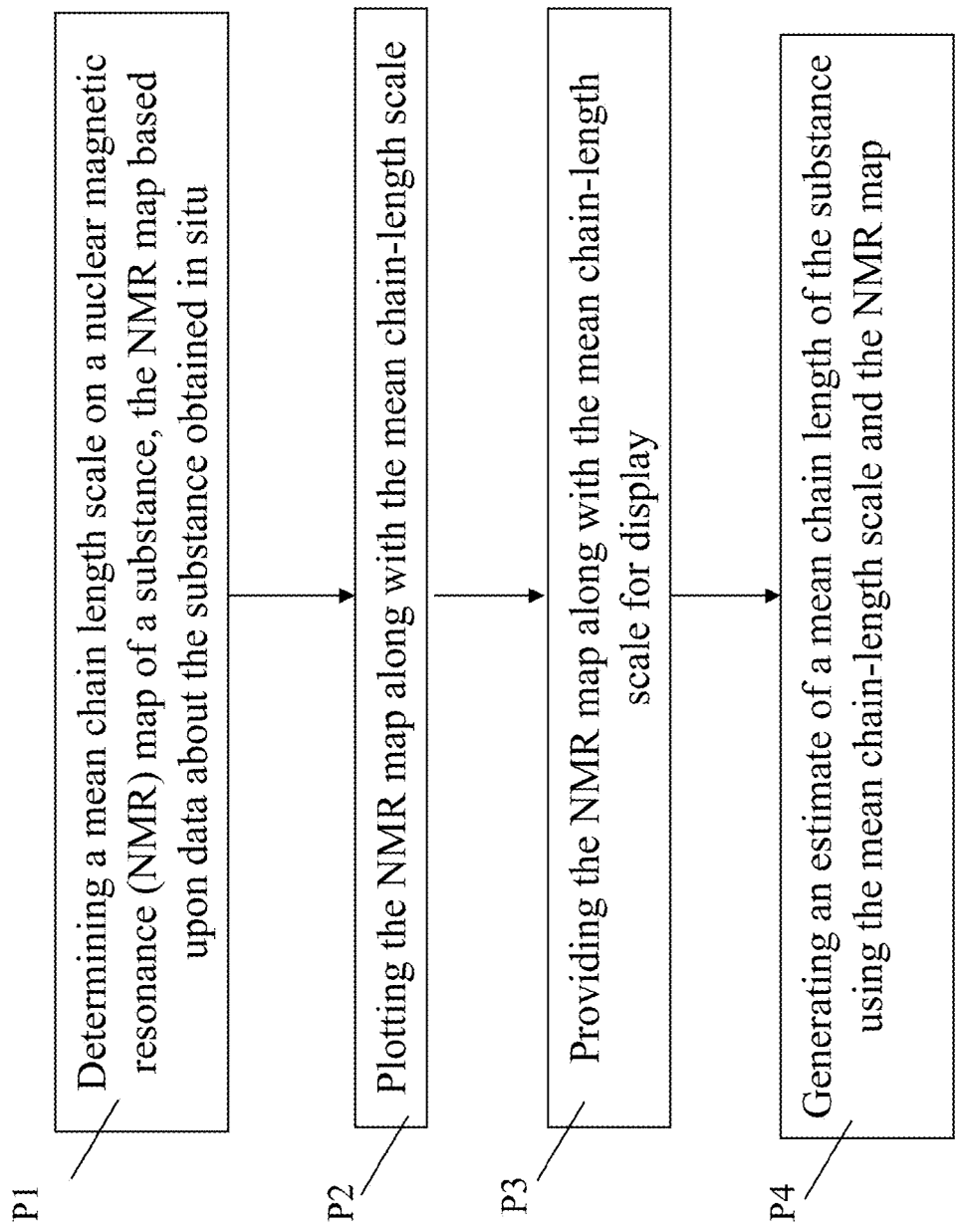
FIGS. 20-22 are flow diagrams illustrating methods according to various embodiments of the disclosure.

FIG. 20 shows a flow diagram illustrating processes in a method according to embodiments of the invention. As described with respect to various aspects of the invention, the method can include the following processes:

Process P1: Determining a mean chain length scale on a nuclear magnetic resonance (NMR) map of a substance, the NMR map based upon data about the substance (e.g., data obtained in situ or otherwise).

Process P2: Plotting the NMR map along with the mean chain-length scale.

Process P3: following process P3, process P2 can include providing the NMR map along with the mean chain-length scale for display.

Process P4: Generating an estimate of a mean chain length of the substance using the mean chain-length scale and the NMR map.

Figure 21:
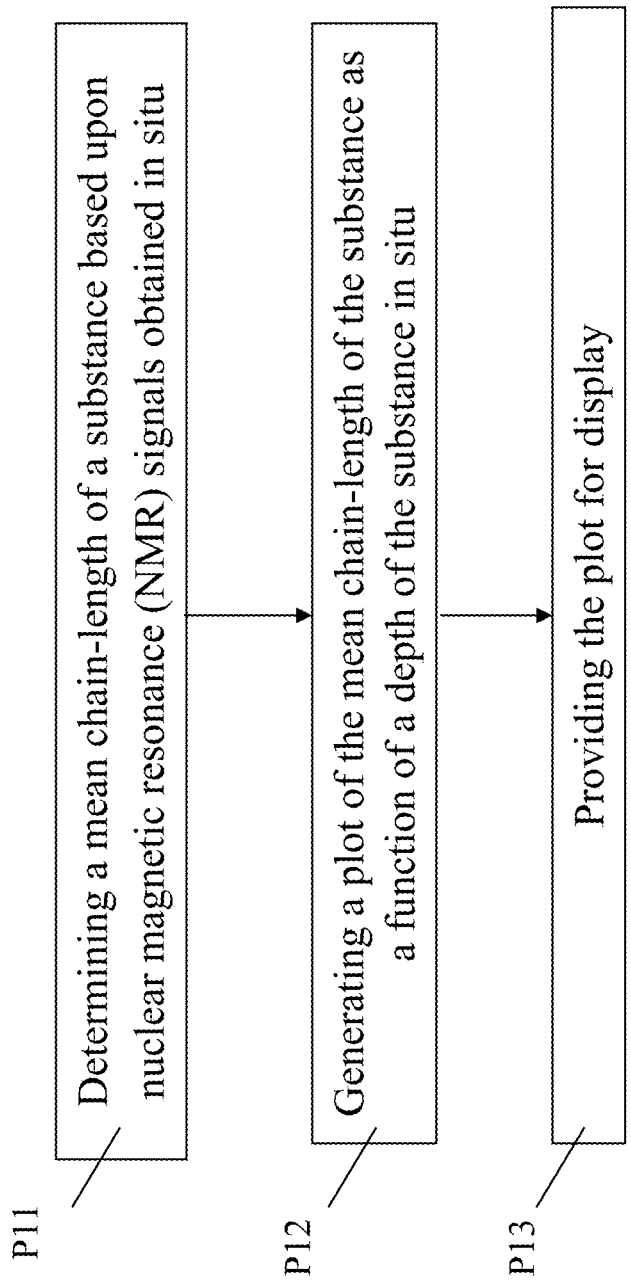

FIG. 21 shows a flow diagram illustrating processes in a method according to other embodiments of the invention. As described with respect to various aspects of the invention, the method can include the following processes:

Process P11: Determining a mean chain-length of a substance based upon nuclear magnetic resonance (NMR) signals obtained, e.g., in situ or otherwise.

Process P12: Generating a plot of the mean chain-length of the substance as a function of a depth of the substance (e.g., in situ or otherwise).

Process P13: Following process P12, Process P13 can include providing the plot for display.

Figure 22:
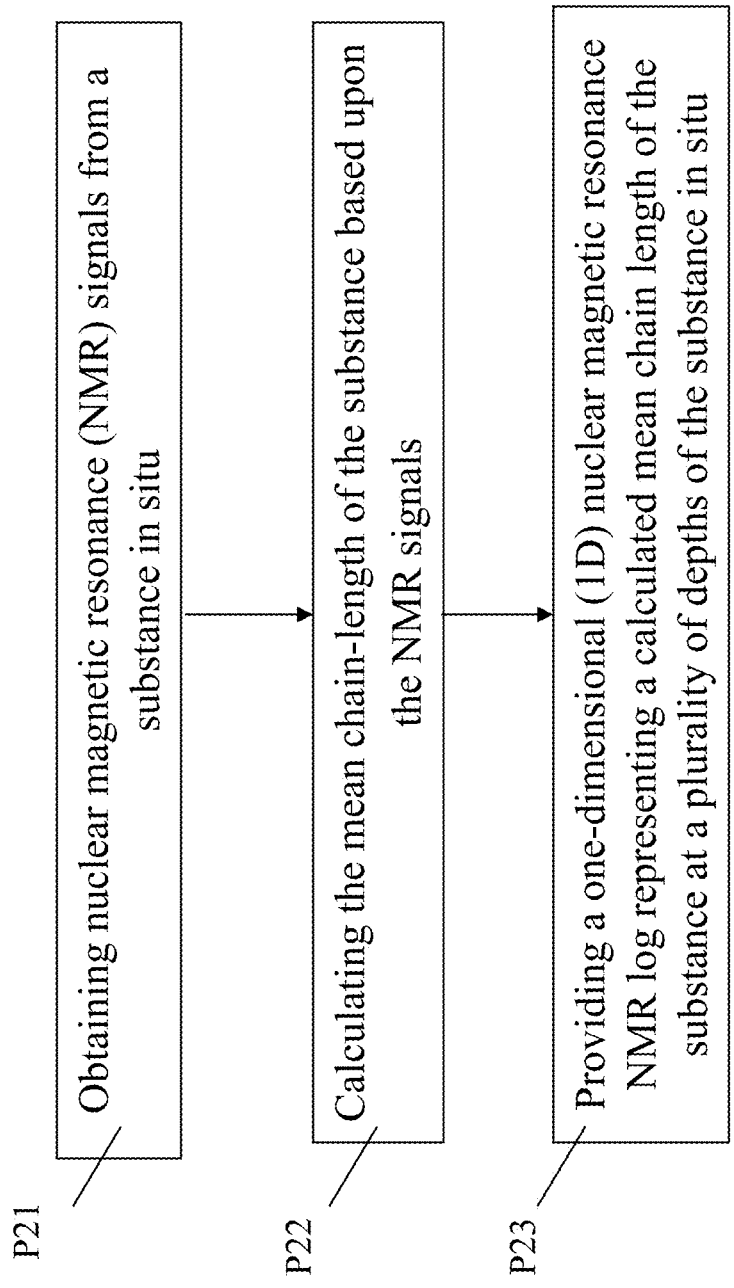

FIG. 22 shows a flow diagram illustrating processes in a method according to other embodiments of the invention. As described with respect to various aspects of the invention, a method can include the following processes:

Process P21: Obtaining nuclear magnetic resonance (NMR) signals from a substance (e.g., in situ or otherwise).

Process P22: Calculating the mean chain-length of the substance based upon the NMR signals.

Process P23: Following calculation of the mean chain length in Process P22, the method can include providing a one-dimensional (1D) nuclear magnetic resonance (NMR) log representing a calculated mean chain length of the substance at a plurality of depths of the substance (e.g., in situ or otherwise). In some cases, the 1D log includes an actuatable region at each of the plurality of depths for providing a two-dimensional (2D) NMR map of the substance at the each of the plurality of depths.

It is understood that the above-noted processes and/or any other processes described herein according to the various aspects of the invention can be implemented utilizing one or more computing devices. In one embodiment discussed further herein, an aspect of the invention includes a computing device configured to perform one or more of the herein-noted processes. In still another embodiment, a computer-readable medium is disclosed including program code having instructions for performing one or more of the herein-noted processes when executed on a computing device.

Figure 23:
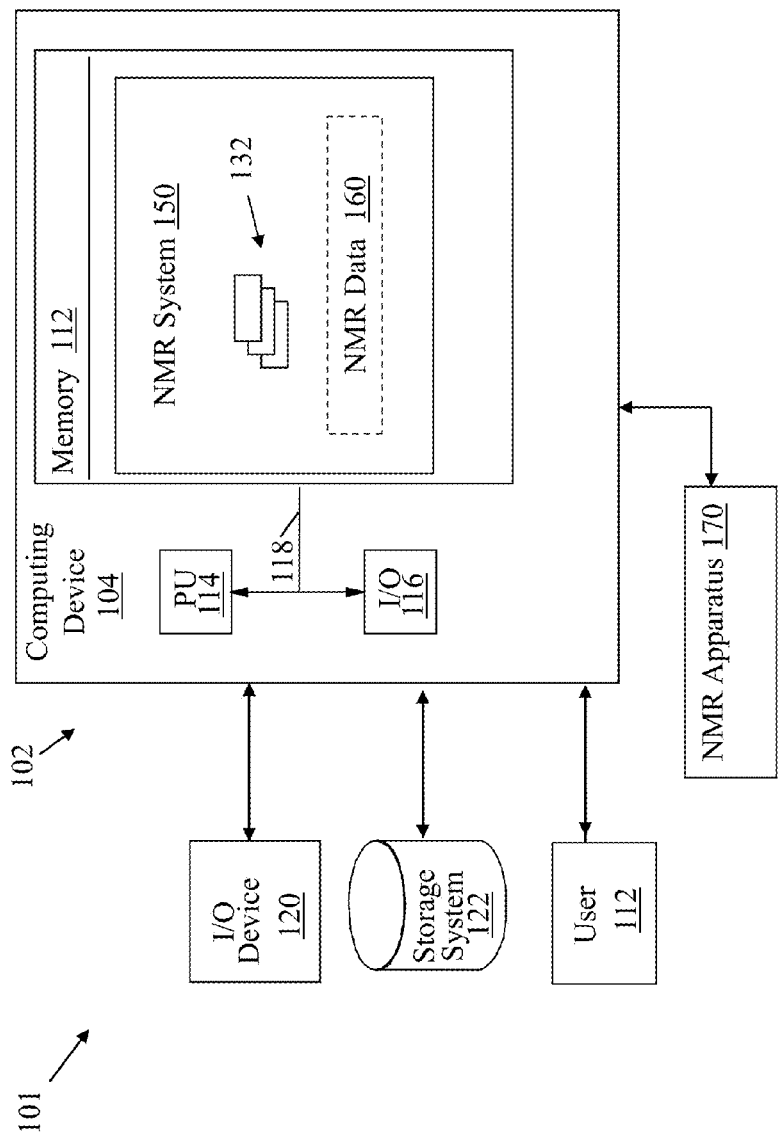
FIG. 23 is an illustrative environment for performing functions according to various aspects of the disclosure.

FIG. 23 depicts an illustrative environment 101 for performing the NMR estimation processes described herein with respect to various embodiments. To this extent, the environment 101 includes a computer system 102 that can perform one or more processes described herein in order to estimate the mean molecular size of a substance in-situ. In particular, the computer system 102 is shown as including an NMR system 150, which makes computer system 102 operable to estimate the mean molecular size of a substance in-situ by performing any/all of the processes described herein and implementing any/all of the embodiments described herein.

The computer system 102 is shown including a processing component 104 (e.g., one or more processors), a storage component 106 (e.g., a storage hierarchy), an in-put/output (I/O) component 108 (e.g., one or more I/O interfaces and/or devices), and a communications pathway 110. In general, the processing component 104 executes program code, such as the NMR system 150, which is at least partially fixed in the storage component 106. While executing program code, the processing component 104 can process data, which can result in reading and/or writing transformed data from/to the storage component 106 and/or the I/O component 108 for further processing. The pathway 110 provides a communications link between each of the components in the computer system 102. The I/O component 108 can comprise one or more human I/O de-vices, which enable a human user 112 to interact with the computer system 102 and/or one or more communications devices to enable a system user 112 to communicate with the computer system 102 using any type of communications link. To this extent, the NMR system 150 can manage a set of interfaces (e.g., graphical user interface(s), application program interface, etc.) that enable human and/or system users 112 to interact with the NMR system 150. Further, the NMR system 150 can manage (e.g., store, retrieve, create, manipulate, organize, present, etc.) data, such as NMR data 160 (including NMR signal data, NMR mapping data, NMR display data, etc.) using any solution. The NMR system 150 can additionally communicate with an NMR apparatus 170, which can include any conventional NMR hardware and/or software capable of generating a static magnetic field, providing pulses according to instructions from the NMR system 150, obtaining NMR signal data, etc.

In any event, the computer system 102 can comprise one or more general purpose computing articles of manufacture (e.g., computing devices) capable of executing program code, such as the NMR system 150, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the NMR system 150 can be embodied as any combination of system software and/or application software.

Further, the NMR system 150 can be implemented using a set of modules 132. In this case, a module 132 can enable the computer system 102 to perform a set of tasks used by the NMR system 150, and can be separately developed and/or implemented apart from other portions of the NMR system 150. As used herein, the term "component" means any configuration of hardware, with or without software, which implements the functionality described in conjunction therewith using any solution, while the term "module" means program code that enables the computer system 102 to implement the functionality described in conjunction therewith using any solution. When fixed in a storage component 106 of a computer sys-tem 102 that includes a processing component 104, a module is a substantial portion of a component that implements the functionality. Regardless, it is understood that two or more components, modules and/or systems may share some/all of their respective hardware and/or software. Further, it is understood that some of the functionality discussed herein may not be implemented or additional functionality may be included as part of the computer system 102.

When the computer system 102 comprises multiple computing devices, each computing device may have only a portion of NMR system 150 fixed thereon (e.g., one or more modules 132). However, it is understood that the computer system 102 and NMR system 150 are only representative of various possible equivalent computer systems that may perform a process described herein. To this extent, in other embodiments, the functionality provided by the computer system 102 and NMR system 150 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 102 includes multiple computing devices, the computing devices can communicate over any type of communications link. Further, while performing a process described herein, the computer system 102 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

The computer system 102 can obtain or provide data, such as NMR data 160 using any solution. The computer system 102 can generate NMR data 160, from one or more data stores, receive NMR data 160, from another system such as an NMR apparatus 170, send NMR data 160 to another system, etc.

While shown and described herein as a method and system for estimating the mean molecular size of a substance in-situ, it is understood that aspects of the invention further provide various alternative embodiments. For example, in one embodiment, the invention provides a computer program fixed in at least one computer-readable medium, which when executed, enables a computer system to estimate the mean molecular size of a substance in-situ. To this extent, the computer-readable medium includes program code, such as the NMR system 150 (FIG. 23), which implements some or all of the processes and/or embodiments described herein. It is understood that the term "computer-readable medium" comprises one or more of any type of tangible medium of expression, now known or later developed, from which a copy of the program code can be perceived, reproduced or otherwise communicated by a computing device. For example, the computer-readable medium can comprise: one or more portable storage articles of manufacture; one or more memory/storage components of a computing device; paper; etc.

In another embodiment, the invention provides a method of providing a copy of program code, such as the NMR system 150 (FIG. 23), which implements some or all of a process described herein. In this case, a computer system can process a copy of program code that implements some or all of a process described herein to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for estimating the mean molecular size of a substance in-situ. In this case, a computer system, such as the computer system 102 (FIG. 23), can be obtained (e.g., created, maintained, made available, etc.) and one or more components for performing a process described herein can be obtained (e.g., created, purchased, used, modified, etc.) and deployed to the computer system. To this extent, the deployment can comprise one or more of (1) installing program code on a computing device; (2) adding one or more computing and/or I/O devices to the computer system; (3) incorporating and/or modifying the computer system to enable it to perform a process described herein; etc.

It is noted that while the above applications relate to oil applications, the method may be adapted for other applications including the medical and food preparation industries, for example.

The invention has been described with reference to particular preferred embodiments, but variations within the spirit and scope of the invention will occur to those skilled in the art. For example, it will be understood that other suitable pulse sequences can be employed. Also, it will be understood that the techniques of the invention can be used in combination with other measurements and techniques, including but not limited to, measurement of relaxation rates, spectroscopy, diffusion constant and other pulse field gradient measurements in a fashion similar to multi-dimensional NMR experiments and analysis.

We claim:

1. A method comprising:
utilizing a relationship between a mean chain length and at least one of (a) a moment of diffusion and (b) a relaxation distribution to create a mean chain-length scale on a nuclear magnetic resonance (NMR) map of molecules within a substance; and
generating a size estimate of the molecules within the substance using the mean chain-length scale and the NMR map.

2. The method of claim 1, further comprising plotting the NMR map along with the mean chain-length scale.

3. The method of claim 2, further comprising providing the NMR map along with the mean chain-length scale for display.

4. The method of claim 3, wherein the mean chain length scale is visually perceivable on the NMR map.

5. The method of claim 1, wherein the NMR map includes a two-dimensional (2D) map.

6. The method of claim 5, wherein the 2D map includes at least one of a diffusion-relaxation or a relaxation-relaxation map.

7. The method of claim 1, wherein the NMR map includes a one-dimensional (1D) distribution plot.

8. The method of claim 1, wherein the NMR map is based upon data about the substance obtained during one of a logging-while-drilling (LWD) or a wireline drilling application.

9. The method of claim 1, wherein the substance includes at least one of: an oil, a gas or an oil-based mud.

10. The method of claim 1, wherein the size estimate of the molecules is selected from the group consisting of: a mean chain length of the molecules, a hydrodynamic radius of the molecules and a hydrocarbon number of the molecules.

11. A method comprising:
determining a molecular size of molecules within a substance based upon nuclear magnetic resonance (NMR) signals for the substance in situ while the substance is within a rock formation;
generating a plot of the molecular size of the molecules within the substance as a function of a depth of the substance; and
providing the plot for display.

12. The method of claim 11, wherein the determining of the molecular size of the molecules within the substance includes calculating the molecular size from at least one of a diffusion measurement or a relaxation measurement of the substance using the NMR signals.

13. The method of claim 12, further comprising determining a fluid volume within the substance from the at least one of the diffusion measurement or the relaxation measurement.

14. The method of claim 13, wherein an intensity of the plot varies based upon the fluid volume of the substance at a corresponding depth.

15. The method of claim 11, wherein the NMR signals include NMR signals corresponding to at least one of: an oil, a gas or an oil-based mud, and wherein the determining includes determining a mean chain-length of the molecules within at least one of: the oil, the gas or the oil-based mud.

16. The method of claim 11, further comprising:
obtaining the NMR signals during one of a logging-while-drilling (LWR) or a wireline drilling process; and
providing the plot for display during the one of the LWR or the wireline drilling process.

17. The method of claim 11, wherein the substance includes a crude oil.

18. The method of claim 17, wherein the substance further includes at least one of gas, water or oil-based mud.

19. The method of claim 18, further comprising separating NMR signals relating to the oil from NMR signals relating to the gas and the water before determining the molecular size of molecules within the oil using the NMR signals relating to the oil.

20. The method of claim 19, wherein the separating of the NMR signals relating to the oil and the NMR signals relating to the gas and the water is performed using an NMR map.

21. The method of claim 11, wherein the molecular size of the molecules is selected from the group consisting of: a mean chain length of the molecules, a chain length distribution of the molecules, a binned molecular size distribution of the molecules, a hydrodynamic radius of the molecules and a hydrocarbon number of the molecules.

22. A method for determining a characteristic of a substance in-situ, the method comprising:
obtaining nuclear magnetic resonance (NMR) signals about the substance while the substance is in situ within a rock formation;
calculating a mean chain-length of molecules within the substance based upon the NMR signals; and
providing a one-dimensional (1D) nuclear magnetic resonance (NMR) log representing a calculated mean chain length of the molecules within the substance at a plurality of depths of the substance,
wherein the one-dimensional NMR log includes an actuatable region at each of the plurality of depths for providing at least one of a two-dimensional (2D) NMR map of the substance or a chain length distribution of the substance at the each of the plurality of depths.

23. The method of claim 22, further comprising displaying the at least one of the 2D NMR map or the chain length distribution of the substance at the selected depth in response to actuation of the actuatable region at the selected depth.

24. The method of claim 22, wherein the obtaining includes detecting the NMR signals during one of a logging-while-drilling (LWD) or a wireline drilling application.

25. The method of claim 24, wherein the NMR signals include NMR signals from at least one of: an oil, a gas or an oil-based mud.

26. The method of claim 25, wherein the calculating includes calculating the mean chain length of the molecules for the at least one of the oil, the gas or the oil-based mud.

27. The method of claim 22, wherein the actuatable region includes at least one of an actuatable button or an icon for initiating the providing of the at least one of the two-dimensional (2D) NMR map or the chain length distribution.

28. The method of claim 22, wherein the 2D NMR map includes a mean chain length scale for generating a size estimate of the molecules within the substance.

* * * * *